United States Patent
Rugel et al.

(10) Patent No.: US 12,131,240 B2
(45) Date of Patent: *Oct. 29, 2024

(54) DATA PROCESSING SYSTEM WITH MACHINE LEARNING ENGINE TO PROVIDE OUTPUT GENERATING FUNCTIONS

(71) Applicant: Allstate Insurance Company, Northbrook, IL (US)

(72) Inventors: John Rugel, Hawthorn Woods, IL (US); Brian Stricker, Northbrook, IL (US); Howard Hayes, Glencoe, IL (US)

(73) Assignee: ALLSTATE INSURANCE COMPANY, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,883

(22) Filed: Feb. 13, 2023

(65) Prior Publication Data
US 2023/0274188 A1    Aug. 31, 2023

Related U.S. Application Data

(63) Continuation of application No. 17/130,156, filed on Dec. 22, 2020, now Pat. No. 11,580,003, which is a
(Continued)

(51) Int. Cl.
*G06N 20/00* (2019.01)
*G06F 11/32* (2006.01)
(Continued)

(52) U.S. Cl.
CPC .......... *G06N 20/00* (2019.01); *G06F 11/321* (2013.01); *G06F 11/3438* (2013.01);
(Continued)

(58) Field of Classification Search
CPC ..... G09B 7/02; G06F 11/261; G06F 17/5022; G06F 17/504
See application file for complete search history.

(56) References Cited

U.S. PATENT DOCUMENTS 5,544,649 A     8/1996  David et al.
5,737,518 A *   4/1998  Grover ................ G06F 11/3672
                                                        714/38.12
(Continued)

OTHER PUBLICATIONS

Dec. 28, 2017—(US) Non-Final Office Action—U.S. Appl. No. 15/727,226, 6 Pages.
(Continued)

*Primary Examiner* — Elias Desta
(74) *Attorney, Agent, or Firm* — Polsinelli PC

(57) ABSTRACT

Systems, methods, computer-readable media, and apparatuses for identifying and executing one or more interactive condition evaluation tests to generate an output are provided. In some examples, user information may be received by a system and one or more interactive condition evaluation tests may be identified. An instruction may be transmitted to a computing device of a user and executed on the computing device to enable functionality of one or more sensors that may be used in the identified tests. A user interface may be generated including instructions for executing the identified tests. Upon initiating a test, data may be collected from one or more sensors in the computing device. The data collected may be transmitted to the system and may be processed using one or more machine learning datasets to generate an output.

20 Claims, 15 Drawing Sheets

Related U.S. Application Data continuation of application No. 16/587,280, filed on Sep. 30, 2019, now Pat. No. 10,878,344, which is a continuation of application No. 16/160,332, filed on Oct. 15, 2018, now Pat. No. 10,445,662, which is a continuation of application No. 15/727,226, filed on Oct. 6, 2017, now Pat. No. 10,140,199, which is a continuation of application No. 15/716,983, filed on Sep. 27, 2017, now abandoned.

(51) Int. Cl.
  *G06F 11/34* (2006.01)
  *G06Q 30/0251* (2023.01)
  *G06Q 30/0601* (2023.01)
  *G06V 30/194* (2022.01)
  *G16H 10/60* (2018.01)

(52) U.S. Cl.
  CPC ..... *G06Q 30/0271* (2013.01); *G06Q 30/0627* (2013.01); *G06V 30/194* (2022.01); *G16H 10/60* (2018.01)

(56) References Cited

U.S. PATENT DOCUMENTS

| | | | |
|---|---|---|---|
| 5,918,222 A | 6/1999 | Fukui et al. | |
| 5,991,734 A | 11/1999 | Moulson | |
| 6,077,304 A | 6/2000 | Kasuya | |
| 6,102,959 A | 8/2000 | Hardin et al. | |
| 6,487,704 B1 | 11/2002 | McNamara et al. | |
| 6,714,975 B1 | 3/2004 | Aggarwal et al. | |
| 6,829,753 B2 | 12/2004 | Lee et al. | |
| 7,010,782 B2 * | 3/2006 | Narayan | H04L 43/50 717/124 |
| 7,130,783 B1 | 10/2006 | Harer et al. | |
| 7,490,085 B2 | 2/2009 | Walker et al. | |
| 8,422,994 B2 | 4/2013 | Rhoads et al. | |
| 8,790,259 B2 | 7/2014 | Katra et al. | |
| 8,909,771 B2 | 12/2014 | Heath | |
| 9,111,455 B2 | 8/2015 | Rogers et al. | |
| 9,798,700 B2 | 10/2017 | Anderson et al. | |
| 10,140,199 B1 | 11/2018 | Rugel et al. | |
| 10,445,662 B2 | 10/2019 | Rugel et al. | |
| 10,540,678 B2 | 1/2020 | Szirtes et al. | |
| 10,839,319 B2 | 11/2020 | Rugel et al. | |
| 10,878,344 B2 | 12/2020 | Rugel et al. | |
| 10,881,348 B2 | 1/2021 | Levine et al. | |
| 11,423,335 B2 | 8/2022 | Rugel et al. | |
| 11,537,935 B2 | 12/2022 | Rugel et al. | |
| 11,580,003 B2 * | 2/2023 | Rugel | G06F 11/321 |
| 2006/0265260 A1 | 11/2006 | Brown et al. | |
| 2010/0083968 A1 | 4/2010 | Wondka et al. | |
| 2011/0301433 A1 | 12/2011 | Sadowsky et al. | |
| 2012/0240206 A1 | 9/2012 | Hoffman | |
| 2013/0246207 A1 | 9/2013 | Novak et al. | |
| 2013/0346115 A1 | 12/2013 | Peak et al. | |
| 2015/0244850 A1 | 8/2015 | Rodriguez et al. | |
| 2015/0248689 A1 | 9/2015 | Paul et al. | |
| 2016/0350274 A1 | 12/2016 | Deng et al. | |
| 2017/0018030 A1 | 1/2017 | Crouspeyre et al. | |
| 2017/0269586 A1 | 9/2017 | D'Andrea et al. | |
| 2019/0095815 A1 | 3/2019 | Rugel et al. | |

OTHER PUBLICATIONS

Dec. 14, 2018 (US) Non-Final Office Action—U.S. Appl. No. 16/160,332, 11 Pages.
Jul. 16, 2018 (US) Notice of Allowance—U.S. Appl. No. 15/727,226, 9 Pages.
Jun. 1, 2018—(US) Final Office Action—U.S. Appl. No. 15/727,226, 7 Pages.
Dec. 31, 2019 (US) Non-Final Office Action—U.S. Appl. No. 16/587,280, 13 Pages.
Sep. 19, 2019 (US) Non-Final Office Action—U.S. Appl. No. 16/382,561, 18 Pages.
Apr. 23, 2020—(US) Final Office Action—U.S. Appl. No. 16/382,561, 14 Pages.
Aug. 7, 2020—(US) Non-Final Office Action—U.S. Appl. No. 15/716,983, 51 Pages.
Jul. 13, 2020 (US) Notice of Allowance—U.S. Appl. No. 16/382,561, 8 Pages.
May 15, 2020 (US) Notice of Allowance—U.S. Appl. No. 16/587,280, 9 Pages.
Sep. 2, 2020 (US) Notice of Allowance—U.S. Appl. No. 16/587,280, 12 Pages.
Feb. 11, 2021—(EP) Office Action—Application No. 168080984, 9 Pages.
Jan. 25, 2021—(US) Non-Final Office Action—U.S. Appl. No. 16/189,374, 45 Pages.
May 13, 2021—(CA) Office Action—Application No. 3,076,898, 3 Pages.
May 3, 2021—(CA) Office Action—App. No. 3076898, 3 pages.
Oct. 28, 2021—(US) Non-Final Office Action—U.S. Appl. No. 17/130,156, 6 Pages.
Extended European Search Report for European Application No. 18863747.4 dated Apr. 20, 2021, 8 pages.
International Preliminary Report on Patentability for International Application No. PCT/US2018/052609, mailed Apr. 9, 2020, 6 pages.
International Search Report and Written Opinion for International Application No. PCT/US2018/052609, mailed Dec. 26, 2018, 7 pages.
International Search Report and Written Opinion for International Application No. PCT/US2020/027395, mailed May 11, 2020, 8 pages.
Dec. 22, 2023—(US) Final Office Action—U.S. Appl. No. 17/892,209, 9 Pages.
Feb. 15, 2024—(US) Final Office Action—U.S. Appl. No. 18/086,194, 20 Pages.
May 15, 2023—(US) Non-Final Office Action—U.S. Appl. No. 18/086,194, 14 Pages.
Communication pursuant to Article 94(3) EPC for Application No. 18 863 747.4 dated Feb. 3, 2023 (8 pages).
May 25, 2023—(US) Non-Final Office Action—U.S. Appl. No. 17/892,209, 14 Pages.

* cited by examiner

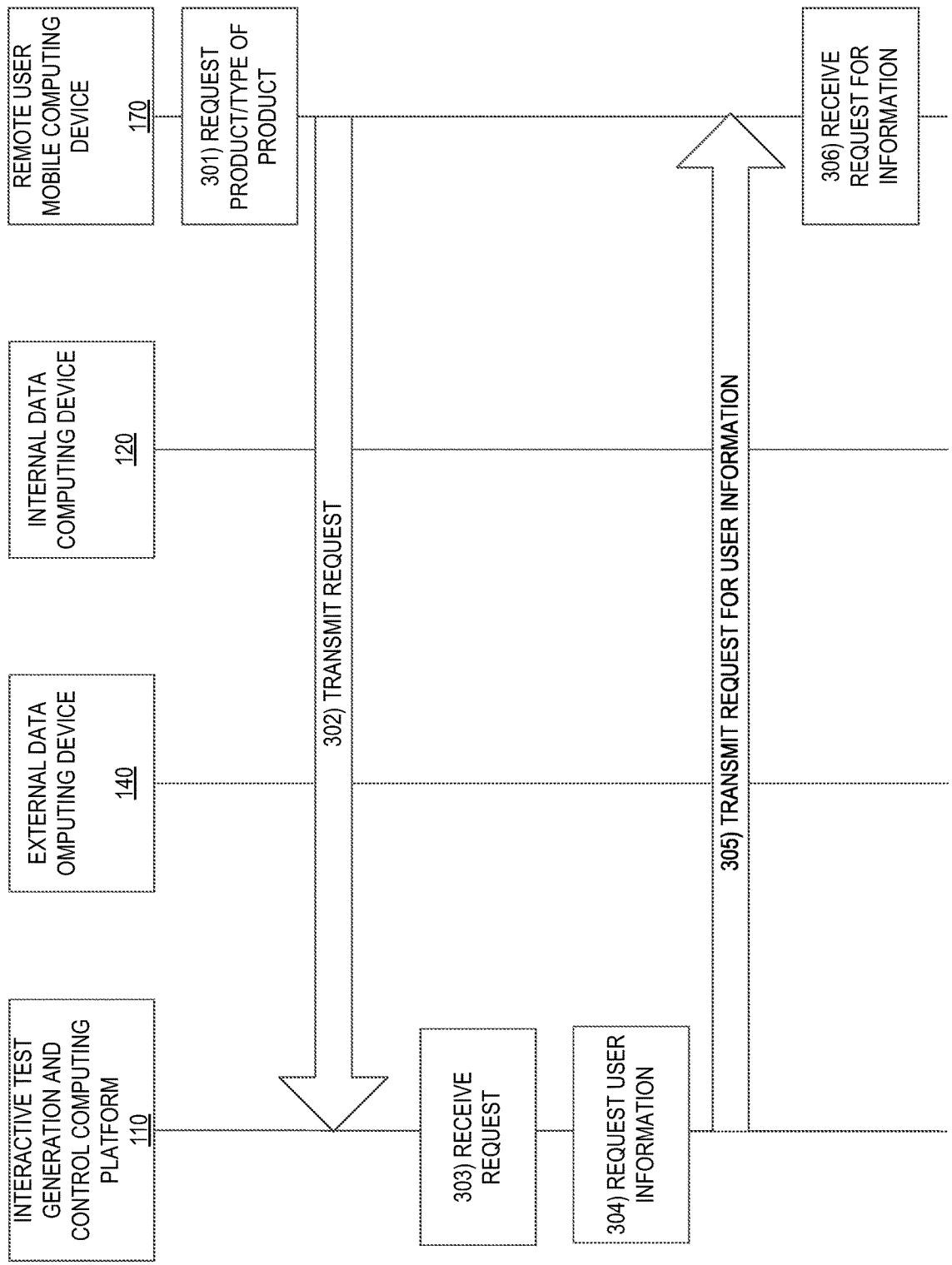

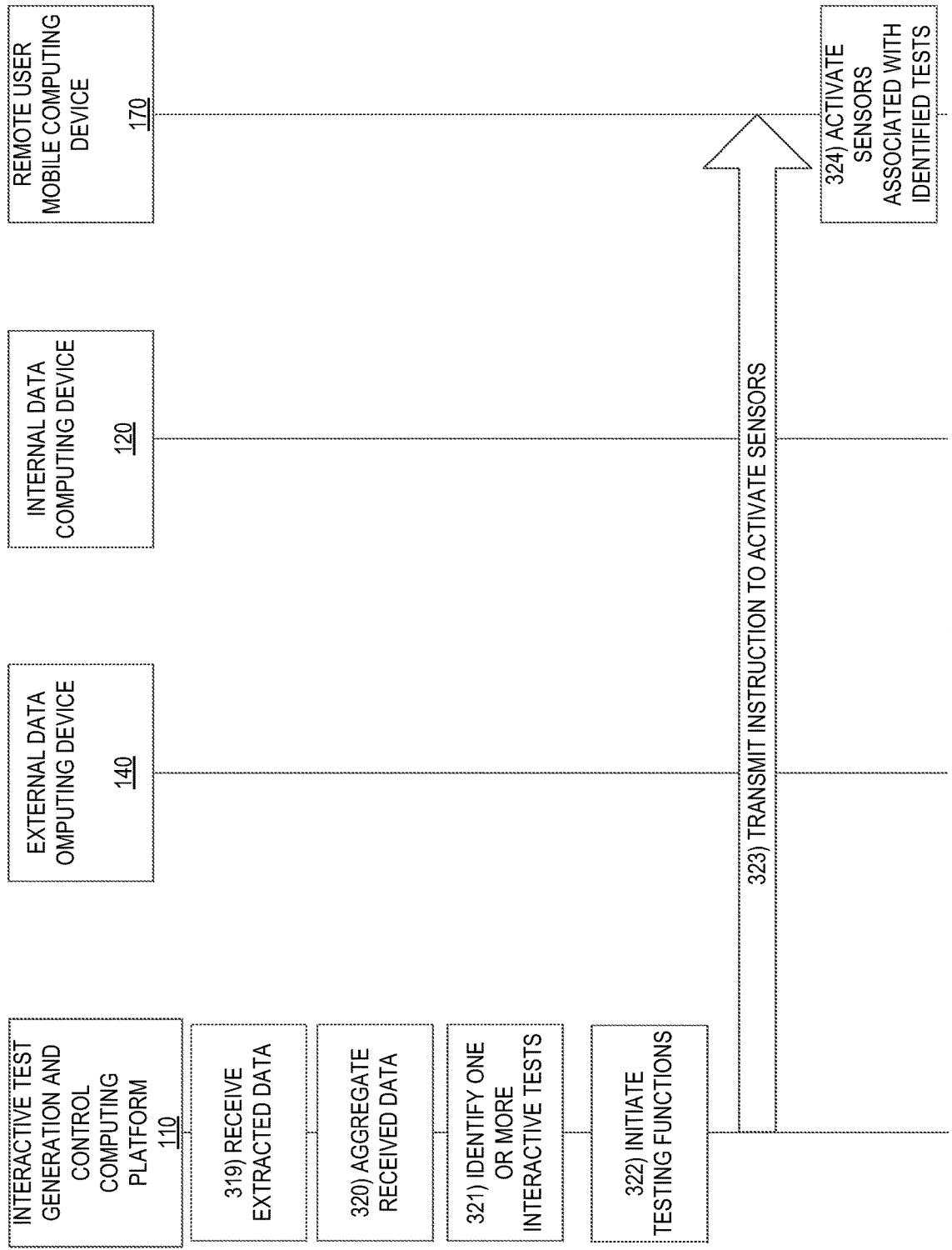

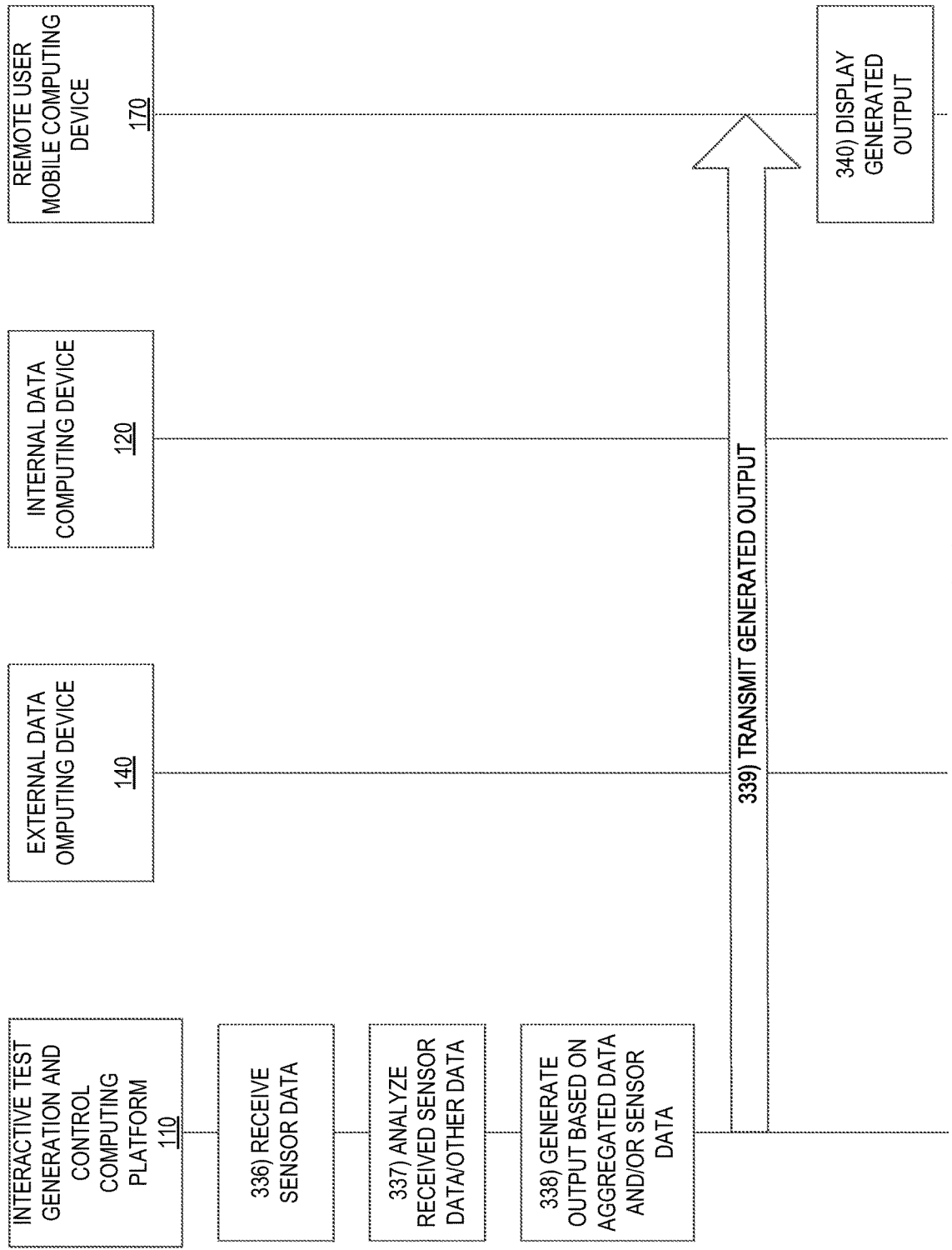

DATA PROCESSING SYSTEM WITH MACHINE LEARNING ENGINE TO PROVIDE OUTPUT GENERATING FUNCTIONS

CROSS REFERENCE TO RELATED APPLICATIONS

This application is a continuation of and claims priority to co-pending U.S. application Ser. No. 17/130,156, filed Dec. 22, 2020, and entitled "Data Processing System with Machine Learning Engine to Provide Output Generating Functions," which is a continuation of and claims priority to U.S. application Ser. No. 16/587,280 (now U.S. Pat. No. 10,878,344), filed Sep. 30, 2019, and entitled "Data Processing System with Machine Learning Engine to Provide Output Generating Functions," which is a continuation of and claims priority to U.S. application Ser. No. 16/160,332 (now U.S. Pat. No. 10,445,662), filed Oct. 15, 2018, and entitled "Data Processing System with Machine Learning Engine to Provide Output Generating Functions," which is a continuation of and claims priority to U.S. application Ser. No. 15/727,226 (now U.S. Pat. No. 10,140,199), filed Oct. 6, 2017, and entitled "Data Processing System with Machine Learning Engine to Provide Output Generating Functions," which is a continuation of and claims priority to co-pending U.S. application Ser. No. 15/716,983, filed Sep. 27, 2017, and entitled "Data Processing System with Machine Learning Engine to Provide Output Generating Functions." Each of these applications is incorporated by reference in its entirety herein.

TECHNICAL FIELD

Aspects of the disclosure generally relate to one or more computer systems, servers, and/or other devices including hardware and/or software. In particular, aspects are directed to executing interactive condition evaluation tests and using machine learning to generate an output.

BACKGROUND

Mobile devices are being used to simplify people's lives around the world. However, it is often difficult to collect sufficient information via user input. In addition, determining an accuracy of information provided by a user can be difficult. Often, confirming accuracy may require in-person communication, additional documentation, and the like. Accordingly, executing a plurality of interactive tests generated by an entity to collect condition data, verify accuracy of data, and the like, may be advantageous.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure relate to methods, computer-readable media, systems, and apparatuses for identifying and executing one or more interactive condition evaluation tests to generate an output.

In some examples, user information may be received by a system, computing device, or the like. Based on the information, one or more interactive condition evaluation tests may be identified. An instruction, command, signal or the like, may be transmitted to a computing device of a user and executed on the computing device to enable functionality of one or more sensors that may be used in the identified interactive condition evaluation tests.

In some examples, a user interface may be generated by the system, computing device, or the like. The user interface may include instructions for executing the identified interactive condition evaluation tests. Upon initiating an interactive condition evaluation test on the computing device of the user, data may be collected from one or more sensors in the computing device.

In some examples, a determination may be made as to whether a triggering event has occurred. If not, data from the sensors may be collected. If so, the interactive condition evaluation test may be terminated and functionality associated with the sensors may be disabled.

In some arrangements, the data collected via the sensors may be transmitted to the system, computing device, or the like, and may be processed using one or more machine learning datasets to generate an output. For instance, the data may be processed to determine an eligibility of user, identify a product or service for the user, or the like.

These and other features and advantages of the disclosure will be apparent from the additional description provided herein.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein:

FIGS. 3A-3G depict an illustrative event sequence for performing interactive condition evaluation test and output generating functions, according to one or more aspects described herein.

DETAILED DESCRIPTION

In the following description of the various embodiments, reference is made to the accompanying drawings, which form a part hereof, and in which is shown by way of illustration, various embodiments of the disclosure that may be practiced. It is to be understood that other embodiments may be utilized.

Mobile devices are being used to perform functions that, at one time, required interaction between users, such as a customer and a vendor, service provider, or the like. However, accuracy of information provided, identity of a user providing input via the mobile device, and the like, may be difficult to confirm. Accordingly, it may be advantageous to identify and execute one or more interactive condition evaluation tests on the mobile device to evaluate a condition of a user, determine eligibility for one or more products or services, and the like.

In some examples, a user may request a product or service (e.g., via a mobile device). The request may be transmitted to a system, computing platform, or the like, which may process the request and transmit a request for additional information. The user may provide the requested additional information via the mobile device. The additional information may include information such as name, age, gender, height, weight, location, and the like.

In some arrangements, based on the information provided, one or more products or services for which the user may be eligible may be identified. Based on the identified one or more products, one or more interactive condition evaluation tests may be identified to determine eligibility of the user.

In some examples, the system may transmit an instruction to the mobile device to enable one or more sensors associated with the identified one or more interactive condition evaluation tests. The one or more tests may then be executed by the mobile device. Data from the one or more sensors may be collected during execution of the test and may be transmitted to the system for processing. In some arrangements, the system may use machine learning to evaluate eligibility of the user (e.g., based on the sensor data and/or other internal and/or external data), generate an output for a user (e.g., a product or service to offer), and the like.

These and other aspects will be described more fully herein.

Figure 1A:
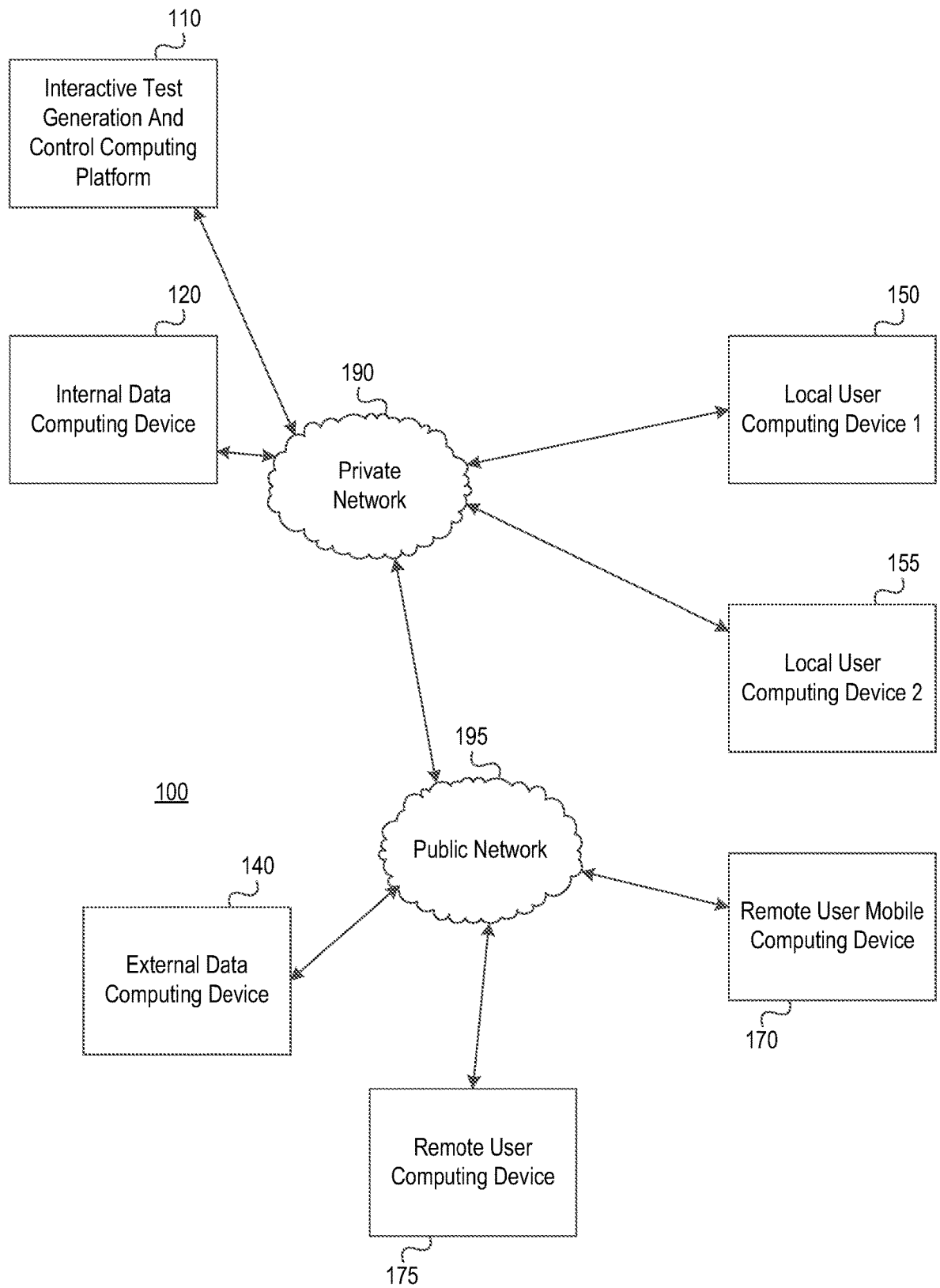
FIGS. 1A and 1B illustrate an illustrative computing environment for implementing interactive condition evaluation test and output generating functions, according to one or more aspects described herein.
Figure 1B:
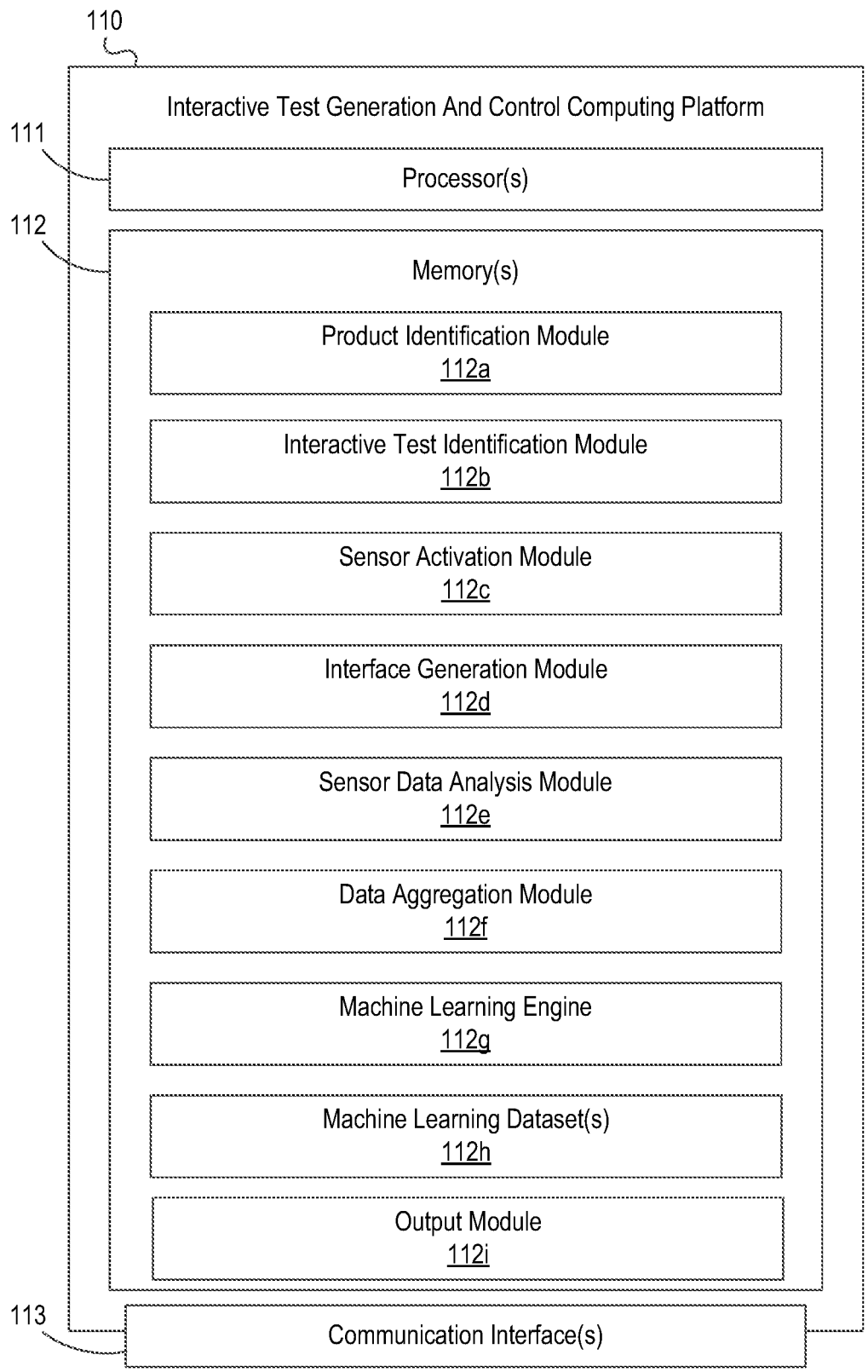

FIGS. 1A-1B depict an illustrative computing environment for implementing and using an interactive test generation and control system in accordance with one or more aspects described herein. Referring to FIG. 1A, computing environment 100 may include one or more computing devices and/or other computing systems. For example, computing environment 100 may include an interactive test generation and control computing platform 110, an internal data computing device 120, a first local user computing device 150, a second local user computing device 155, an external data computing device 140, a remote user mobile computing device 170, and a remote user computing device 175.

Interactive test generation and control computing platform 110 may be configured to host and/or execute one or more modules including instructions for providing various interactive condition evaluation test functions and/or factor prediction functions. In some examples, interactive test generation and control computing platform 110 may be configured to receive data from a plurality of disparate sources, aggregated data, using a machine learning engine, generate one or more predictions, generate and initiate one or more interactive condition evaluation tests, and the like.

One or more aspects described herein may be performed by one or more applications downloaded or otherwise provided to a computing device (such as first local user computing device 150, second local user computing device 155, remote user mobile computing device 170, remote user computing device 175, or the like) and executing thereon. In some examples, the one or more applications (or portions thereof) may execute in a background of the device.

Although various devices in the interactive test generation and control processing system are shown and described as separate devices, one or more of interactive test generation and control computing platform 110, internal data computing device 120, external data computing device 140, first local user computing device 150, second local user computing device 155, remote user mobile computing device 170, and/or remote user computing device 175, may be part of a single computing device without departing from the invention.

Internal data computing device 120 may have, store and/or include data obtained by an entity implementing the interactive test generation and control computing platform 110 and/or stored by the entity. In some examples, internal data computing device 120 may include data associated with customers, one or more insurance claims, accident histories and associated damages, costs, etc., user information, and the like. In some examples, internal data computing device 120 may include multiple computing devices storing various different types of data. In other examples, internal data computing device 120 may store the various types of data. In still other examples, internal data computing device 120 may query databases in one or more other computing devices, systems, or the like, to obtain data that may be used in one or more processes described herein.

External data computing device 140 may have, store and/or include data from outside of or external to the entity. For instance, external data computing device 140 may store or provide access to publicly available information, such as weather, traffic, population, demographic information, and the like. Additionally or alternatively, external data computing device 140 may store or provide access to data related to spending habits of one or more users (e.g., types of purchases made, amounts, locations of purchases, and the like). In still other examples, external data computing device 140 may store or provide access to data related to behaviors of users, such as frequency of gym visits, data collected by a wearable fitness device, and the like. Various other types of information may be accessed via the external data computing device 140 without departing from the invention. In some examples, external data computing device 140 may access information from various sources, such as via public network 195.

Local user computing device 150, 155, internal data computing system 120, external data computing system 140, remote user mobile computing device 170, and remote user computing device 175 may be configured to communicate with and/or connect to one or more computing devices or systems shown in FIG. 1A. For instance, local user computing device 150, 155 and/or internal data computing device 120 may communicate with one or more computing systems or devices via network 190, while remote user mobile computing device 170, remote user computing device 175, and/or external data computing device 140 may communicate with one or more computing systems or devices via network 195. The local and remote user computing devices may be used to configure one or more aspects of interactive test generation and control computing platform 110, display one or more notifications, execute one or more interactive condition evaluation tests, capture data associated with one or more interactive condition evaluation tests, display outputs, and the like.

In one or more arrangements, internal data computing device 120, local user computing device 150, local user computing device 155, external data computing device 140, remote user mobile computing device 170, and/or remote user computing device 175 may be any type of computing device or combination of devices capable of performing the particular functions described herein. For example, internal data computing device 120, local user computing device 150, local user computing device 155, external data computing device 140, remote user mobile computing device 170, and/or remote user computing device 175 may, in some instances, be and/or include server computers, desktop computers, laptop computers, tablet computers, smart phones, or the like that may include one or more processors, memories, communication interfaces, storage devices, and/or other components. As noted above, and as illustrated in greater detail below, any and/or all of interactive test generation and control computing platform 110, internal data computing device 120, local user computing device 150, local user computing device 155, external data computing device 140, remote user mobile computing device 170, and/or remote user computing device 175 may, in some instances, be or include special-purpose computing devices configured to perform specific functions.

Computing environment 100 also may include one or more computing platforms. For example, and as noted above, computing environment 100 may include interactive test generation and control computer platform 110. As illustrated in greater detail below, interactive test generation and control computer platform 110 may include one or more computing devices configured to perform one or more of the functions described herein. For example, interactive test generation and control computer platform 110 may have or include one or more computers (e.g., laptop computers, desktop computers, tablet computers, servers, server blades, or the like).

As mentioned above, computing environment 100 also may include one or more networks, which may interconnect one or more of interactive test generation and control computer platform 110, internal data computing device 120, local user computing device 150, local user computing device 155, external data computing device 140, remote user mobile computing device 170, and/or remote user computing device 175. For example, computing environment 100 may include private network 190 and public network 195. Private network 190 and/or public network 195 may include one or more sub-networks (e.g., Local Area Networks (LANs), Wide Area Networks (WANs), or the like). Private network 190 may be associated with a particular organization (e.g., a corporation, financial institution, educational institution, governmental institution, or the like) and may interconnect one or more computing devices associated with the organization. For example, interactive test generation and control computer platform 110, internal data computing device 120, local user computing device 150, and/or local user computing device 155, may be associated with an organization (e.g., a financial institution), and private network 190 may be associated with and/or operated by the organization, and may include one or more networks (e.g., LANs, WANs, virtual private networks (VPNs), or the like) that interconnect interactive test generation and control computer platform 110, internal data computing device 120, local user computing device 150, and/or local user computing device 155, and one or more other computing devices and/or computer systems that are used by, operated by, and/or otherwise associated with the organization. Public network 195 may connect private network 190 and/or one or more computing devices connected thereto (e.g., interactive test generation and control computer platform 110, internal data computing device 120, local user computing device 150, local user computing device 155) with one or more networks and/or computing devices that are not associated with the organization. For example, external data computing device 140, remote user mobile computing device 170, and/or remote user computing device 175 might not be associated with an organization that operates private network 190 (e.g., because external data computing device 140, remote user mobile computing device 170 and remote user computing device 175 may be owned, operated, and/or serviced by one or more entities different from the organization that operates private network 190, such as one or more customers of the organization, public or government entities, and/or vendors of the organization, rather than being owned and/or operated by the organization itself or an employee or affiliate of the organization), and public network 195 may include one or more networks (e.g., the internet) that connect external data computing device 140, remote user mobile computing device 170 and remote user computing device 175 to private network 190 and/or one or more computing devices connected thereto (e.g., interactive test generation and control computer platform 110, internal data computing device 120, local user computing device 150, and/or local user computing device 155).

Referring to FIG. 1B, interactive test generation and control computing platform 110 may include one or more processors 111, memory 112, and communication interface 113. A data bus may interconnect processor(s) 111, memory 112, and communication interface 113. Communication interface 113 may be a network interface configured to support communication between interactive test generation and control computing platform 110 and one or more networks (e.g., private network 190, public network 195, or the like). Memory 112 may include one or more program modules having instructions that when executed by processor(s) 111 cause interactive test generation and control computing platform 110 to perform one or more functions described herein and/or one or more databases that may store and/or otherwise maintain information which may be used by such program modules and/or processor(s) 111. In some instances, the one or more program modules and/or databases may be stored by and/or maintained in different memory units of interactive test generation and control computing platform 110 and/or by different computing devices that may form and/or otherwise make up interactive test generation and control computing platform 110.

For example, memory 112 may have, store, and/or include a product identification module 112a. The product identification module 112a may store instructions and/or data that may cause or enable the interactive test generation and control computing platform 110 to receive data from, for examples, local user computing device 150, local user computing device 155, remote user mobile computing device 170, and/or remote user computing device 175 that may include a request for a product or service, information about a user requesting the product or service or for whom the product or service is being requested, and the like. In some examples, the requested product may be a life or other insurance product. In some arrangements, information received may include name and/or other identifier of a user, age, gender, height, weight, and the like. The information may be transmitted from the local user computing device 150, 155, remote user mobile computing device 170, remote user computing device 175, or the like, to the interactive test generation and control computing platform 110 and may be processed by the product identification module 112a to identify one or more products (e.g., a life insurance policy) to offer or recommend to the user. In some examples, interactive tests used to determine eligibility for the one or more products may be identified based on the identified one or more products, as will be discussed more fully herein.

Memory 112 may further have, store and/or include an interactive test identification module 112b. The interactive test identification module 112b may store instructions and/or data that may cause or enable the interactive test generation and control computing platform 110 to generate or identify one or more interactive condition evaluation tests based on one or more products identified by the product identification module 112a. For instance, one or more interactive condition evaluation tests may be identified for execution by a user. The results of the identified one or more interactive condition evaluation tests may then be used, either alone or in conjunction with other data, to determine whether a user is eligible for the one or more products, a cost associated with the products, a deductible associated with the products, a discount or refund that may be available to the user if the user accepts the product, and the like. Some example tests may include mobility tests, cognitive skills tests, breathing or other lung capacity tests, and the like. In some examples, the tests may be executed by the user on a mobile device, such as remote user mobile computing device 170, or remote user computing device 175. Types of tests, execution of tests, and the like, will be discussed more fully herein.

Memory 112 may further have, store and/or include a sensor activation module 112c. Sensor activation module 112c may store instructions and/or data that may cause or enable the interactive test generation and control computing platform 110 to activate or enable one or more sensors of a plurality of sensors in a user computing device, such as remote user mobile computing device 170, remote user computing device 175, or the like. Some example sensors may include accelerometers, global positioning system (GPS) sensors, gyroscopes, pressure sensors, humidity sensors, pedometer, heart rate sensors, pulse sensors, breathing sensors, one or more cameras or other image capturing devices, and the like. Sensors may also include components of the computing device, such as a usage monitor, or the like) that may record or detect operation of the device, applications executed, contact with a display of the device, user input, and the like. Upon identifying one or more interactive condition evaluation tests to be executed, the sensor activation module 112c may transmit a signal, instruction or command to the computing device (e.g., remote user mobile computing device 170, remote user computing device 175, or the like) activating and/or enabling one or more sensors. In some examples, the sensors activated or enabled may be sensors identified for use with the identified one or more interactive condition evaluation tests. In some arrangements, the sensors activated or enabled may be fewer than all sensors associated with the computing device.

Memory 112 may further have, store, and/or include an interface generation module 112d. The interface generation module 112d may store instructions and/or data that may cause or enable the interactive test generation and control computing platform 110 to generate one or more user interfaces associated with each identified interactive condition evaluation test. For example, for each test identified for execution, the interface generation module 112d may generate one or more user interfaces including, for example, information associated with each test, instructions for initiating and/or performing each test, and the like. The interface generation module 112d may transmit the user interfaces to a user computing device, such as remote user mobile computing device 170, remote user computing device 175, or the like, and may cause the user interface(s) to display on the device.

Memory 112 may further have, store and/or include a sensor data analysis module 112e. Sensor data analysis module 112e may store instructions and/or data that may cause or enable the interactive test generation and control computing platform 110 to receive sensor data from a computing device executing one or more interactive condition evaluation tests (e.g., remote user mobile computing device 170, remote user computing device 175, or the like) and analyze the sensor data. In some examples, the sensor data analysis module 112e may receive raw sensor data and may process the data (e.g., filter, smooth, or the like) to identify data for analysis (e.g., data to provide the most accurate analysis available). In some examples, one or more machine learning datasets may be used to evaluate data from the sensor data analysis module 112e to evaluate a condition of the user executing the test associated with the sensor data, as will be discussed more fully herein. In some examples, sensor data may include an outcome of a mobility test (e.g., walk a predetermined distance, walk a predetermined time on a treadmill at a designated speed, or the like), an outcome of a reflex analysis (e.g., how quickly a user responds to a prompt on the device), an outcome of one or more cognitive skills tests (e.g., questions directed to evaluating memory, recognition, and the like), an outcome of a lung capacity test (e.g., as determined from a force on which a user exhales onto the computing device from a predetermined distance), and the like.

Memory 112 may further have, store and/or include a data aggregation module 112f. Data aggregation module 112f may store instructions and/or data that may cause or enable the interactive test generation and control computing platform 110 to receive data from a plurality of sources. For instance, data may be received from one or more internal sources (e.g., internal data computing device 120) and/or from one or more external sources (e.g., external data computing device 140). The data may include data associated with users (e.g., names, addresses, ages, genders, and the like), demographic information, locality information, behavioral information (e.g., exercise habits, each habits, etc.), purchase habits or history, medical information, and the like. Some or all of the data may be collected with permission of the user. In some examples, one or more machine learning datasets may be used to evaluate the aggregated data, either alone or in conjunction with other data (e.g., sensor data, data from one or more interactive condition evaluation tests, or the like) to determine one or more outputs, as will be discussed more fully herein.

Interactive test generation and control computing platform 110 may further have, store, and/or include a machine learning engine 112g and machine learning datasets 112h. Machine learning engine 112g and machine learning datasets 112h may store instructions and/or data that cause or enable interactive test generation and control computing platform 110 to evaluate data, such as sensor data or other data from a computing device executing one or more interactive condition evaluation tests, aggregated data from internal sources, external sources, and the like, to generate or determine one or more outputs (e.g., by output generation module 112i). The machine learning datasets 112h may be generated based on analyzed data (e.g., data from previously executed interactive condition evaluation tests, historical data from internal and/or external sources, and the like), raw data, and/or received from one or more outside sources.

The machine learning engine 112g may receive data (e.g., data collected during one or more interactive condition evaluate tests executed by and received from, for example, remote user mobile computing device 170, remote user computing device 175, or the like, internal data computing device 120, external data computing device 140, and the like) and, using one or more machine learning algorithms, may generate one or more machine learning datasets 112h. Various machine learning algorithms may be used without departing from the invention, such as supervised learning algorithms, unsupervised learning algorithms, regression algorithms (e.g., linear regression, logistic regression, and the like), instance based algorithms (e.g., learning vector quantization, locally weighted learning, and the like), regularization algorithms (e.g., ridge regression, least-angle regression, and the like), decision tree algorithms, Bayesian algorithms, clustering algorithms, artificial neural network algorithms, and the like. Additional or alternative machine learning algorithms may be used without departing from the invention. In some examples, the machine learning engine 112g may analyze data to identify patterns of activity, sequences of activity, and the like, to generate one or more machine learning datasets 112h.

The machine learning datasets 112h may include machine learning data linking one or more outcomes of an interactive condition evaluation test, types or amounts of sensor data, historical behavioral data, transaction data, health data, or the like (or combinations thereof) to one or more outputs. For instance, data may be used to generate one or more machine learning datasets 112h linking data from interactive condition evaluation tests, internal user data, external user data, and the like, to outputs, such as a mortality rate, likelihood of developing one or more illnesses or diseases, and the like. This information may be used to evaluate a risk associated with a user requesting a product or service (e.g., a life insurance product or service) to determine a premium of an insurance policy, a discount, rebate or other incentive to offer to the user, and the like. In some examples, the information may be used to evaluate risk associated with a user requesting an auto or home product or service (e.g., insurance product). The information may be used to determine a premium, deductible, incentive, or the like.

The machine learning datasets 112h may be updated and/or validated based on later-received data. For instance, as additional interactive condition evaluation tests are executed, data is collected or received from internal data computing device 120, external data computing device 140, and the like, the machine learning datasets 112h may be validated and/or updated based on the newly received information. Accordingly, the system may continuously refine determinations, outputs, and the like.

The machine learning datasets 112h may be used by, for example, an output generation module 112i stored or included in memory 112. The output generation module 112i may store instructions and/or data configured to cause or enable the interactive test generation and control computing platform 110 to generate one or more outputs based on the machine learning dataset 112h analysis of data (e.g., sensor data, aggregate data, and the like). For instance, as discussed above, the output generation module 112i may generate one or more premiums, discounts, incentives, or the like, related to a product identified for a user, requested by a user, or the like. In some examples, the output generation module 112i may transmit the generated output to a computing device, such as remote user mobile computing device 170, remote user computing device 175, or the like, and may cause the generated output to display on the device. In some arrangements, the output may be transmitted to the computing device from which the user requested a product, on which the one or more interactive condition evaluation tests were executed, or the like.

Figure 2:
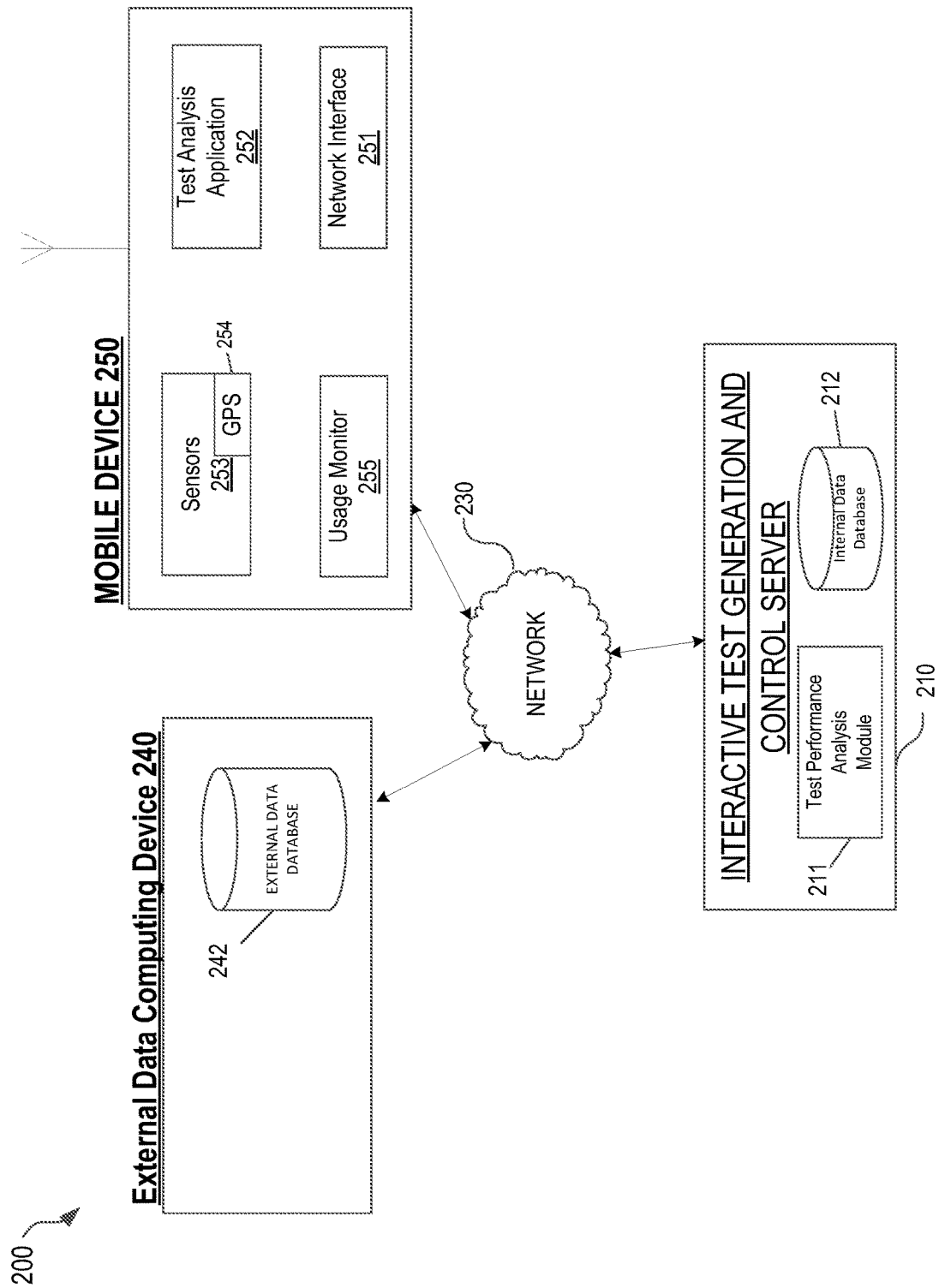
FIG. 2 illustrates an example interactive test generation and control computing system, according to one or more aspects described herein.

FIG. 2 is a diagram of an illustrative interactive test generation and control system 200 including an interactive test generation and control server 210, an external computing device 240, a mobile device 250, and additional related components. Each component shown in FIG. 2 may be implemented in hardware, software, or a combination of the two. Additionally, each component of the interactive test generation and control system 200 may include a computing device (or system) having some or all of the structural components described herein for computing device 901 in FIG. 9. The interactive test generation and control system 200 may also include or be in communication with one or more computing platforms, servers, devices, and the like, shown and described with respect to FIGS. 1A and 1B.

One or more components shown in FIG. 2, interactive test generation and control server 210, external data computing device 240, and/or mobile device 250 may communicate with each other via wireless networks or wired connections, and each may communicate additional mobile computing devices, other remote user computing devices (e.g., remote user computing device 170) and/or a number of external computer servers, devices, etc. 210, 240, over one or more communication networks 230. In some examples, the mobile computing device 250 may be paired (e.g., via Bluetooth™ technology) to one or more other devices (e.g., another user personal mobile computing device, such as a wearable device, tablet, etc.). If the device is no longer in proximity to be paired (e.g., mobile computing device 250 is no longer near enough to another user personal mobile computing device to be paired) a notification may be generated and displayed on the device 250 (e.g., to indicate that you may have left a device behind).

As discussed herein, the components of interactive test generation and control system 200, operating individually or using communication and collaborative interaction, may perform such features and functions such as identifying one or more products or services, identifying one or more interactive condition evaluation tests, executing one or more interactive condition evaluation tests, collecting data associated with one or more interactive condition evaluation tests, retrieving data from one or more internal and/or external sources, generating an output, and the like.

Interactive test generation and control system 200 may include one or more mobile devices 250. Mobile device 250 may be, for example, smartphones or other mobile phones, personal digital assistants (PDAs), tablet computers, laptop computers, wearable devices such as smart watches and fitness monitors, and the like. Mobile device 250 may include some or all of the elements described herein with respect to the computing device 901.

Mobile device 250 may include a network interface 251, which may include various network interface hardware (e.g., adapters, modems, wireless transceivers, etc.) and software components to enable mobile device 250 to communicate with interactive test generation and control server 210, external computing device 240, and various other external computing devices. One or more specialized software applications, such as test analysis application 252 may be stored in the memory of the mobile device 250. The test analysis application(s) 252 may be received via network interface 251 from the interactive test generation and control server 210, or other application providers (e.g., public or private application stores). Certain test analysis applications 252 might not include user interface screens while other applications 252 may include user interface screens that support user interaction. Such applications 252 may be configured to run as user-initiated applications or as background applications. The memory of mobile device 250 also may include databases configured to receive and store sensor data received from mobile device sensors, usage type, application usage data, and the like. Although aspects of the test analysis software application(s) 252 are described as executing on mobile device 250, in various other implementations, some or all of the test analysis functionality described herein may be implemented by interactive test generation and control server 210.

As discussed herein, mobile device 250 may include various components configured to generate and/or receive data associated with execution of one or more interactive condition evaluation tests by or on the mobile device 250, and/or data associated with usage of the mobile device 250. For example, using data from sensors 253 (e.g., 1-axis, 2-axis, or 3-axis accelerometers, compasses, speedometers, vibration sensors, pressure sensors, gyroscopic sensors, etc.) and/or GPS receivers or other location-based services (LBS) 254, an application 252 (or other device or module, e.g., interactive test generation and control server 210) may determine movement of the mobile device 250, evaluate actions performed with or on the mobile device 250, and the like. The sensors 253 and/or GPS receiver or LBS component 254 of a mobile device 250 may also be used to determine speeds (e.g., walking pace, running pace, etc.), force on mobile device, response times for providing input to the mobile device, and the like.

Mobile device 250 may further include a usage monitor 255. The usage monitor may be a device (e.g., including a processor, etc.) and may include hardware and/or software configured to monitor various aspects of the usage of the mobile device 250. For instance, the usage monitor 255 may monitor a number of minutes, hours, or the like the device is in use (e.g., based on factors such as device being illuminated, user interacting with or looking at the device, etc.). Further, the usage monitor 255 may monitor which applications are used above a threshold amount of time in a predetermined time period (e.g., one day, one week, one month, or the like). In still other examples, the usage monitor 255 may determine a type of motion or speed of motion associated with movement of the mobile device 250, whether the device is maintained within a case, and the like. Additional aspects of device usage may be monitored without departing from the invention. Data related to usage of the mobile device 250 may be used to determine one or more outputs (e.g., may indicate decreased mobility, inactive lifestyle, and the like).

The mobile device 250 may be configured to establish communication interactive test generation and control server 210 via one or more wireless networks (e.g., network 230).

The system 200 may further include an external data computing device 240. External data computing device 240 may store or receive data from one or more external data sources, such as user information, health information, automotive information (e.g., driving behaviors, operational parameters, make, model, trim, etc.), transaction information, user behavioral information, and the like. This information may be aggregated and process, for instance, by interactive test generation and control server 240, to generate one or more outputs. The external data computing device 240 may include an external data database that may store data from one or more external sources for use in generating one or more outputs.

Figure 9:
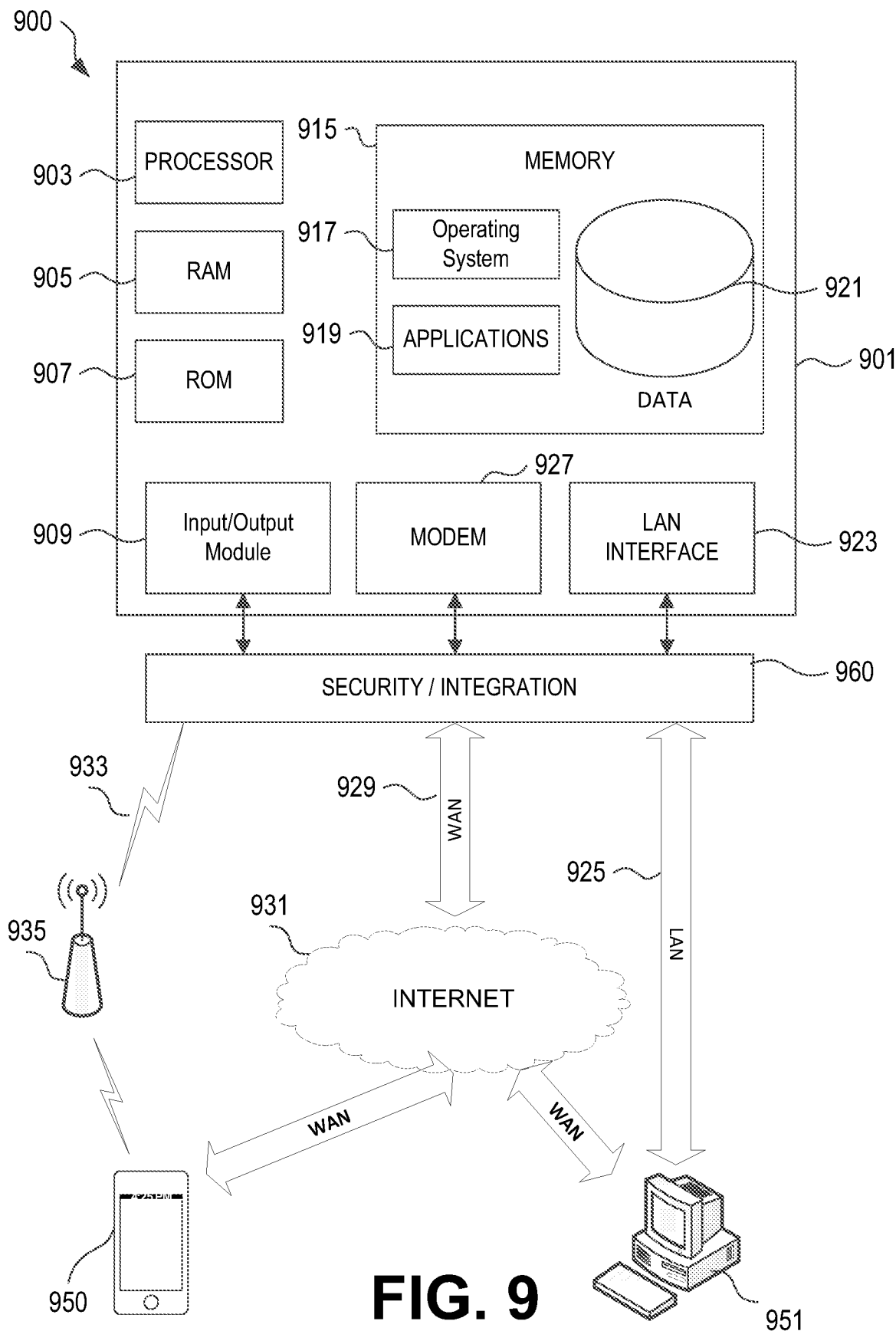
FIG. 9 illustrates a network environment and computing systems that may be used to implement aspects of the disclosure.

The system 200 also may include one or more external servers, such as interactive test generation and control server 210 which may contain some or all of the hardware/software components as the computing device 901 depicted in FIG. 9.

The interactive test generation and control server 210 may include some or all of the components and/or functionality described with respect to FIGS. 1A and 1B. The server 210 may include one or more databases 212 configured to store data associated with, for example, data internal to the entity (e.g., user or customer data, historical data relating to claims, accidents, and the like), that may be used to evaluate risk. Further, the server 210 may include test performance analysis module 211 which may provide some or all of the operations and/or functionality described with respect to FIGS. 1A and 1B.

FIGS. 3A-3G illustrate one example event sequence for executing one or more interactive condition evaluation tests and determining an output in accordance with one or more aspects described herein. The sequence illustrated in FIGS. 3A-3G is merely one example sequence and various other events may be included, or events shown may be omitted, without departing from the invention.

With reference to FIG. 3A, in step 301, a request for a particular product or service, or type of product or service may be received by a user computing device, such as remote user mobile computing device 170. The request may include a request to purchase the particular product or service. In some examples, the request may include information associated with a user for whom the request is made (e.g., name, contact information, and the like).

In step 302, the request may be transmitted from the remote user mobile computing device 170 to the interactive test generation and control computing platform 110. The request may be received by the interactive test generation and control computing platform 110 in step 303 and may process the request.

In step 304, a request for additional user information may be generated. The request may include a request for information associated with the particular user, such as age, gender, location, occupation, tobacco usage, and the like. In step 305, the request for additional user information may be transmitted to the remote user mobile computing device 170 and, in step 306, the request for additional information may be received by the remote user mobile computing device 170.

Figure 3B:
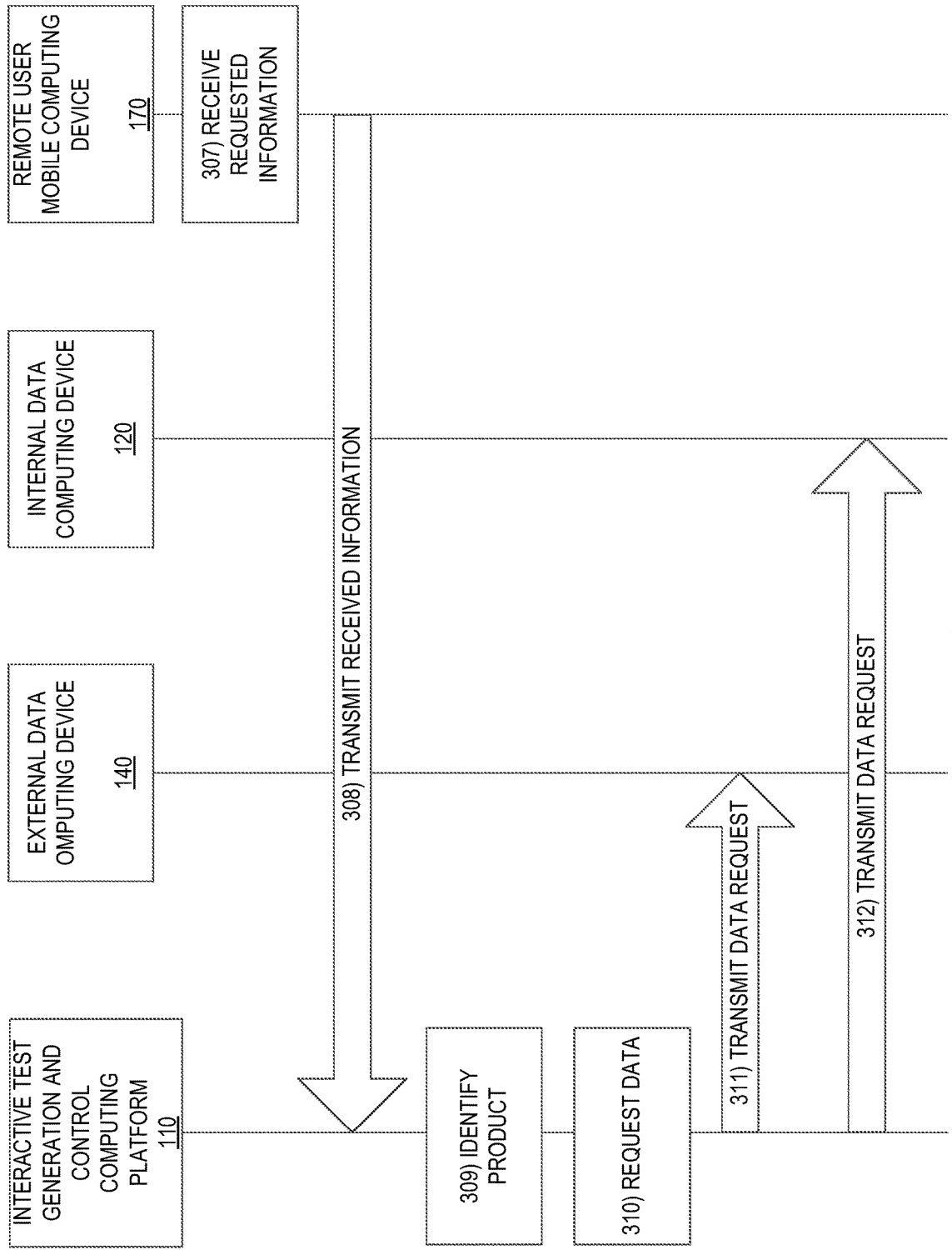

With reference to FIG. 3B, in step 307, the requested additional user information may be received by the remote user mobile computing device 170. In step 308, the received additional information may be transmitted to the interactive test generation and control computing platform 110.

In step 309, the received additional information may be processed to identify one or more products or services to offer to the user that meet the request provided by the user (e.g., if the user has requested a life insurance policy, the computing platform 110 may identify one or more life insurance policies that may be suitable for the user based on the user information and that may be offered to the user).

In step 310, a request for data may be generated. For instance, the interactive test generation and control computing platform 110 may generate one or more requests for data associated with the user. The requests may include data related to health information of the user, spending habits or other transaction information, lifestyle information, driving behaviors, insurance claim information, and the like. The data requests may be transmitted to an external data computing device 140 in step 311 and/or an internal data computing device 120 in step 312. In some examples, requests for data may be transmitted to additional computing devices. In some arrangements, the requests for data may include a name or other unique identifier of a user that may be used as input in a query to identify the desired data.

Figure 3C:
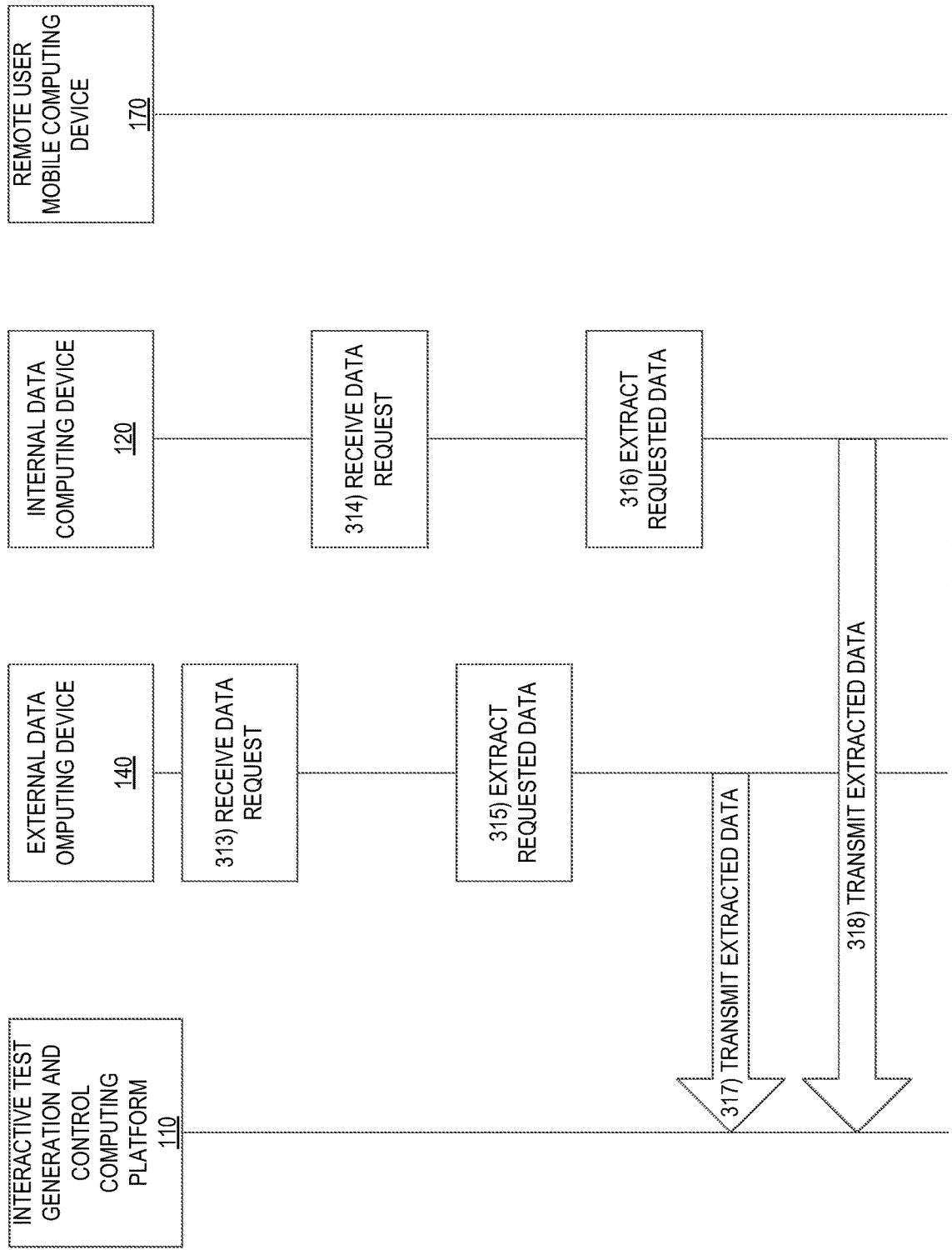

With reference to FIG. 3C, the request for data may be received by the external data computing device 140 in step 313 and the internal data computing device 120 in step 314. In steps 315 and 316, the requested data may be extracted from the external data computing device 140 and internal data computing device 120, respectively. In step 317, data extracted from the external data computing device 140 may be transmitted to the interactive test generation and control computing platform 110. In step 318, data extracted from the internal data computing device 120 may be transmitted to the interactive test generation and control computing platform 110.

With reference to FIG. 3D, in step 319, the extracted data may be received and, in step 320, the extracted data may be aggregated. In some examples, step 320 of aggregating the data may be optional.

In step 321, one or more interactive condition evaluation tests to determine eligibility for the one or more identified products may be identified. For instance, based on the one or more products or services identified for the user, one or more interactive condition evaluation tests may be identified. In some examples, a plurality of different types of interactive condition evaluation tests may be stored and, in step 321, one or more of the plurality of tests may be selected or identified for execution on the remote user mobile computing device 170. Particular types of tests will be discussed more fully herein.

For instance, data associated with the user may be used to identify one or more products to offer to the user and the identified one or more products may be used to identify one or more interactive condition evaluation tests to execute. In some examples, user information (e.g., age, health information, and the like) may also be used in identifying one or more interactive condition evaluation tests to and/or in determining parameters of one or more interactive condition evaluation tests. For instance, if the system identifies a first test as a timed treadmill test in which a user must walk on a treadmill for a predetermined distance (as measured by the remote user mobile computing device 170), the required distance may be modified based on an age of a user and/or an expected time (or time to fit into a particular category) may be modified based on the age of the user. Accordingly, in one example, a 65 year old user requesting life insurance may be given a test having a shorter distance or a long expected time than a 25 year old user requesting life insurance.

In step 322, one or more interactive condition evaluation test functions may be initiated by the interactive test generation and control computing platform 110. For instance, upon identifying one or more tests for execution, one or more functions associated with administering the tests (e.g., generating interfaces including instructions, transmitting interfaces, processing received data, and the like) may be enabled or activated by or within the interactive test generation and control computing platform 110. In some examples, upon completion of the testing process (e.g., upon generating an output) the enabled or activated functions may be disabled or deactivated in order to conserve computing resources.

In step 323, an instruction to activate one or more sensors in the remote user mobile computing device 170 may be generated and transmitted to the remote user mobile computing device 170. For instance, upon identifying one or more interactive condition evaluation tests for execution by the remote user mobile computing device 170, the interactive test generation and control computing platform 110 may identify one or more sensors within the remote user mobile computing device 170 that may be used to collect data associated with the identified tests and may transmit an instruction to the remote user mobile computing device 170 to activate or enable the identified sensors. In step 324, the instruction may be received by the remote user mobile computing device 170 and may be executed to activate the identified sensors.

Figure 3E:
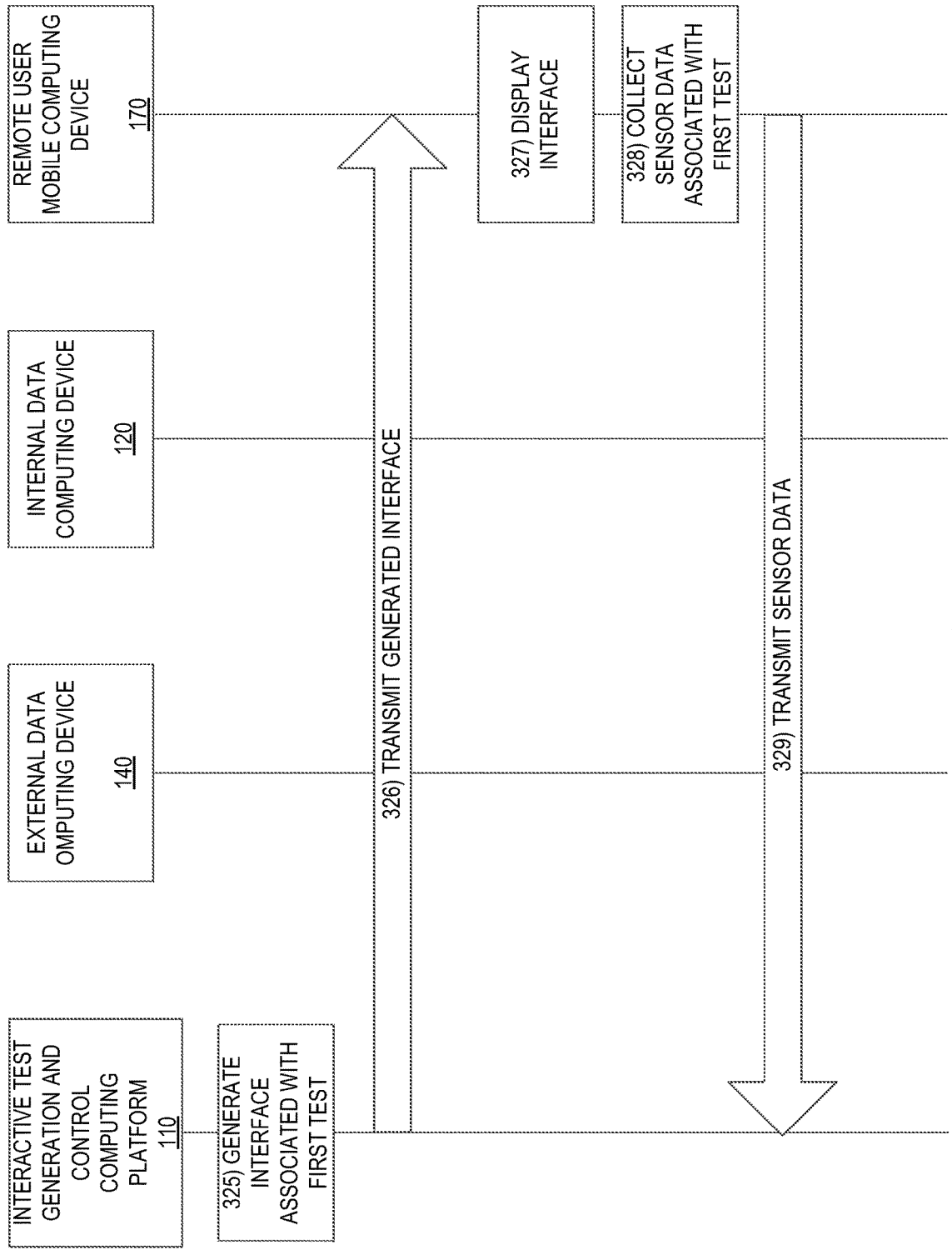

With reference to FIG. 3E, in step 325, a user interface associated with a first test of the identified one or more interactive condition evaluation tests may be generated. In some examples, the user interface may include instructions for executing the first test. In step 326, the generated user interface may be transmitted to the remote user mobile computing device 170 and, in step 327, the user interface may be displayed on a display of the remote user mobile computing device 170.

In step 328, the first test may be initiated and sensor data associated with the first test may be collected. For instance, data from one or more sensors monitoring movement, speed, position, and the like, of the remote user mobile computing device 170 may be collected. In some examples, data may be collected based on interaction with one or more user interfaces (e.g., response times, etc.). In step 329, the sensor data may be transmitted from the remote user mobile computing device 170 to the interactive test generation and control computing platform 110.

Figure 3F:
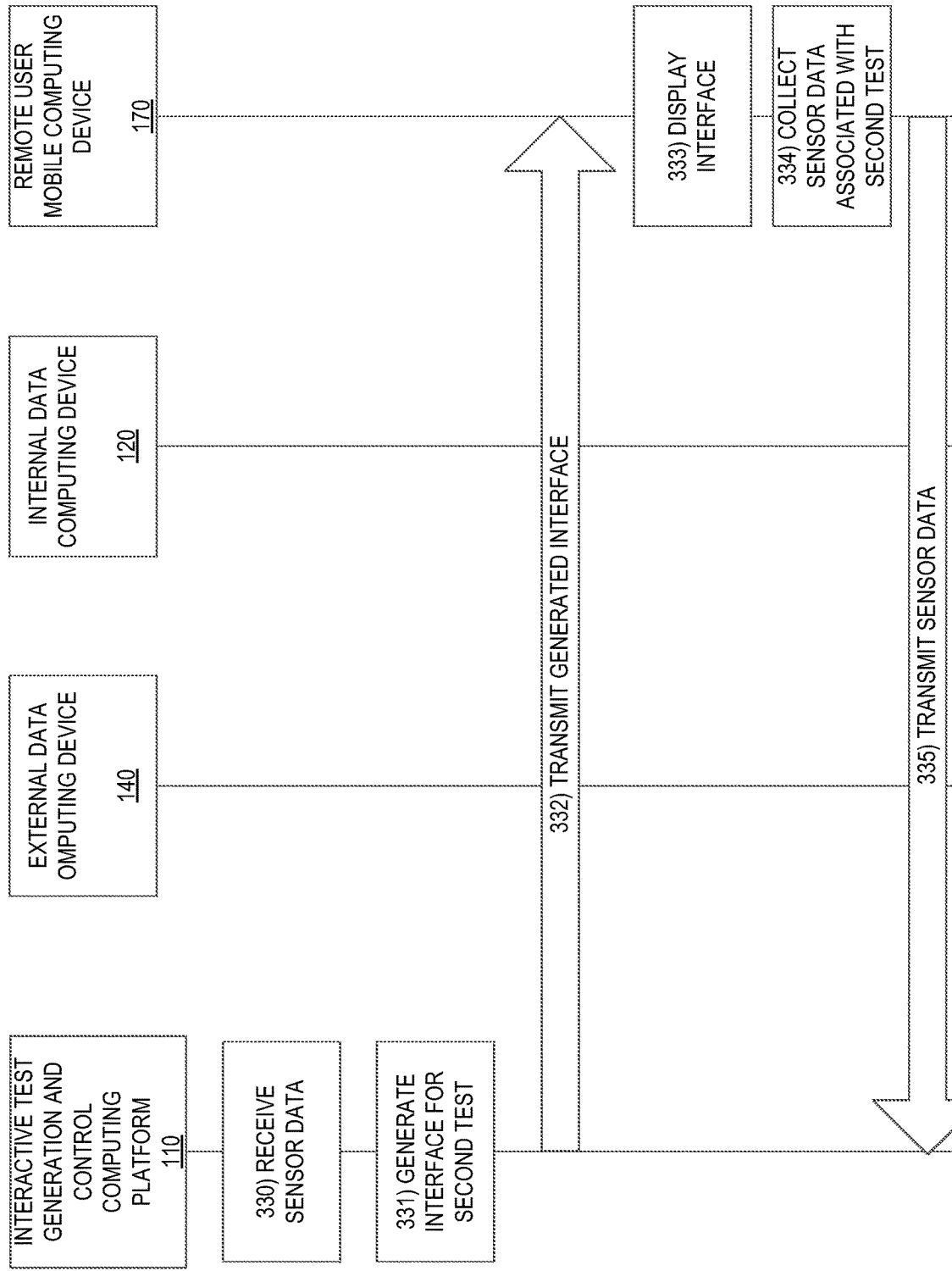

With reference to FIG. 3F, the sensor data may be received in step 330. In step 331, if additional tests have been identified for execution, a user interface for a second interactive condition evaluation test may be generated. The user interface may include instructions and/or parameters for executing the second interactive condition evaluation test by or with the remote user mobile computing device 170.

In step 332, the user interface may be transmitted to the remote user mobile computing device 170 and, in step 333, the user interface may be displayed on a display of the remote user mobile computing device 170.

In step 334, sensor data associated with execution of the second interactive condition evaluation test may be collected and, in step 335, the collected sensor data may be transmitted to the interactive test generation and control computing platform 110.

With reference to FIG. 3G, in step 336, sensor data associated with the second interactive condition evaluation test may be received. In step 337, the received sensor data (e.g., from the first test, second test, and any other tests) and/or other data (e.g., data from internal sources 120, data from external sources 140, and the like) may be analyzed. In some examples, analyzing the data may include comparing the data to one or more machine learning datasets.

In step 338, an output may be generated based on the analysis of the sensor data and/or other data. For instance, based on the comparison of the data to the one or more machine learning datasets, an output may be generated. In some examples, the generated output may be a life insurance policy having parameters generated based on the analysis of the data. Additionally or alternatively, a premium associated with the life insurance policy may also be generated as an output. In still other examples, a discount, rebate or other incentive may be generated as an output. For instance, if tobacco use is detected, the system may generate an incentive such as a rebate if the user stops tobacco use and submits to a subsequent interactive condition evaluation test to confirm the tobacco use has stopped.

Various other outputs may be generated without departing from the invention.

In step 339, the generated output may be transmitted to, for instance, the remote user mobile computing device 170. Additionally or alternatively, the generated output may be transmitted to another computing device, such as local computing device 150, local computing device 155, and/or remote user computing device 175.

In step 340, the generated output may be displayed on the remote user mobile computing device 170. In some examples, displaying the generated output may include an option to accept the offered product or service, identified parameters, and the like. Selection of this option may bind the user and product or service provider. Accordingly, by executing the interactive condition evaluation tests and providing results to the interactive test generation and control computing platform, the user may obtain the desired product or service without submitting to a formal underwriting process, which may include a physical examination, and the like.

Figure 4:
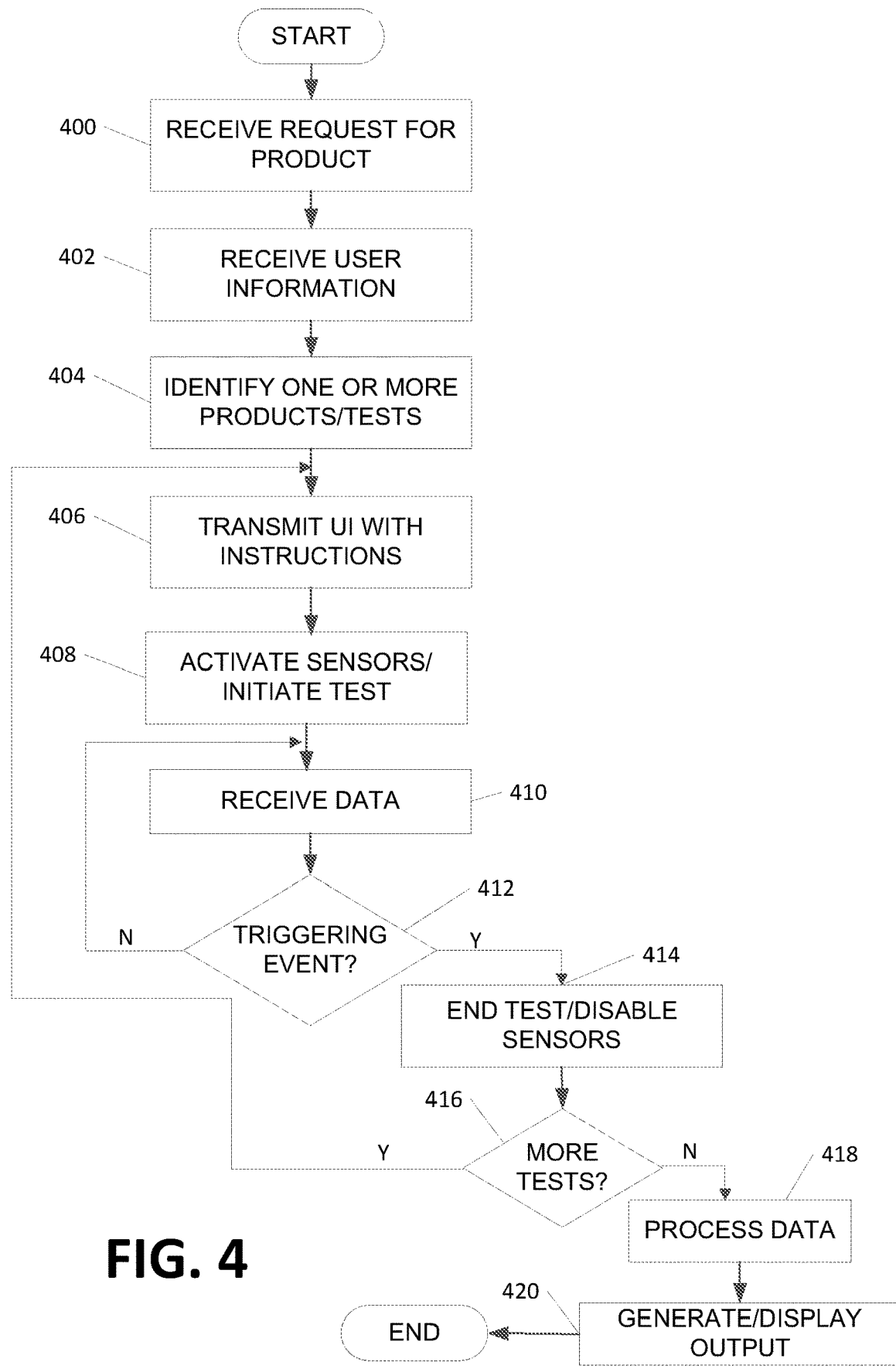
FIG. 4 illustrates one example flow chart illustrating an example method of executing one or more interactive condition evaluation tests and generating an output, according to one or more aspects described herein.

FIG. 4 illustrates one example process for generating and evaluating interactive condition evaluations tests and/or other data, to generate an output according to one or more aspects described herein. The steps described with respect to FIG. 4 may be performed by one or more of the various devices described herein, such as the interactive test generation and control computing platform 110, the interactive test generation and control server 210, remote user mobile computing device, and the like. In some examples, one or more of the processes or steps described may be performed in real-time or near real-time.

In step 400, a request for a product may be received. In some examples, the request may be received from a user computing device, such as remote user mobile computing device 170. In step 402, user information may be received from, for instance, the remote user mobile computing device 170. In some examples, the user information may include information requested by, for instance, the interactive test generation and control computing platform 110 and may include information such as age, gender, location, and the like.

In step 404, one or more products and interactive tests may be identified. For instance, the received user information may be used to identify one or more products for which the user may be eligible and that meet the request for the product. Based on the identified one or more products, one or more interactive condition evaluation tests may be identified to determine whether the user is eligible for the identified one or more products.

In step 406, a user interface including instructions for executing an interactive condition evaluation test of the identified one or more interactive condition evaluation tests may be generated and transmitted to, for instance, the remote user mobile computing device 170. In step 408, an instruction or command may be transmitted to, for instance, the remote user mobile computing device 170 to activate one or more sensors associated with the interactive condition evaluation test and initiate the interactive condition evaluation test.

In step 410, data may be collected from one or more sensors, monitoring or usage devices, or the like, associated with the remote user mobile computing device 170. For instance, data from sensors associated with the interactive condition evaluation test being executed may be collected and/or transmitted to the interactive test generation and control computing platform 110.

In step 412, a determination is made as to whether a triggering event has occurred. In some examples, a triggering event may include an indication that a test is complete, that one or more parameters or criteria of the test have been met, that a threshold amount of data has been received, or the like. If, in step 412, a triggering event has not occurred, the process may return to step 410 to continue collecting data.

If, in step 412, a triggering event has occurred, the interactive condition evaluation test may be terminated (e.g., the interactive test generation and control computing platform 110 may transmit an instruction, signal or command to terminate the test and, in some examples, disable or deactivate one or more sensors activated for execution of the interactive condition evaluation test.

In step 416, a determination may be made as to whether there are additional tests identified for execution (e.g., a second or more test identified in step 404). If so, the process may return to step 406 and may generate and transmit instructions for a second test, etc.

If, in step 416, a determination is made that there are no additional tests identified for execution, the collected data may be processed in step 418. In some examples, the collected data may be processed itself. In other examples, the collected data may be processed with other data, such as aggregated data from one or more other sources. Processing the data may include comparing the data to one or more machine learning datasets to predict or identify an output. In step 420, an output may be generated, transmitted to and displayed, for example, via a display of remote user mobile computing device 170. In some examples, the output may include an insurance product recommendation, a premium for an insurance product, a discount or other incentive, or the like.

Figure 5:
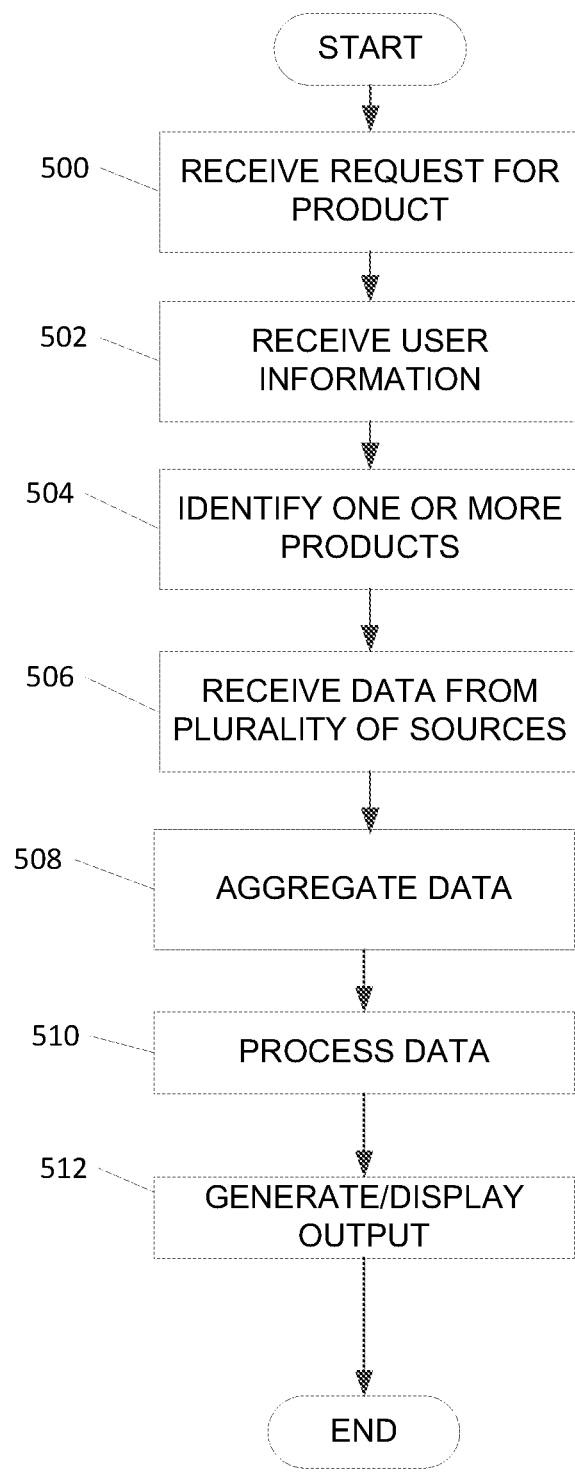
FIG. 5 illustrates one example flow chart illustrating example output generating functions, according to one or more aspects described herein.

FIG. 5 illustrates one example process for aggregating data from disparate sources to generate an output according to one or more aspects described herein. The steps described with respect to FIG. 5 may be performed by one or more of the various devices described herein, such as the interactive test generation and control computing platform 110, the interactive test generation and control server 210, remote user mobile computing device, and the like. In some examples, one or more of the processes or steps described may be performed in real-time or near real-time.

In step 500, a request for a product may be received. In some examples, the request may be received from a user computing device, such as remote user mobile computing device 170. In step 502, user information may be received from, for instance, the remote user mobile computing device 170. In some examples, the user information may include information requested by, for instance, the interactive test generation and control computing platform 110 and may include information such as age, gender, location, and the like.

In step 504, one or more products may be identified. For instance, the received user information may be used to identify one or more products for which the user may be eligible and that meet the request for the product. In step 506, data may be received from a plurality of sources. For instance, data may be received from sources internal to an entity and/or sources external to an entity. For example, data may be received from one or more internal sources and may include data associated with a user, such as age, gender, location, whether the user is a homeowner, marital status, insurance history, claim history, driving behaviors, and the like.

In some examples, data may be received from one or more external sources and may include data associated with the user, such as medical/prescription history, consumer data such as transaction or purchase history, behavioral information (e.g., gym membership, gym usage, and the like), as well as other external data. In some examples, at least some data may be received with permission of the user.

In some examples, data received may be data associated with a computing device associated with the user. For instance, the interactive test generation and control computing platform 110 may receive data associated with movement of a user's mobile computing device, how often the device is in motion, type or motion or speed (e.g., walking vs. driving), types of applications often executed on the mobile device, and the like.

In step 508, the received data may be aggregated and, in step 510, the data may be processed to determine whether a user is eligible for the one or more products identified. In some examples, processing the data may include using one or more machine learning datasets to determine eligibility, generate an output, and the like. In step 512, an output may be generated and or displayed, for instance, on a user computing device.

Figure 6:
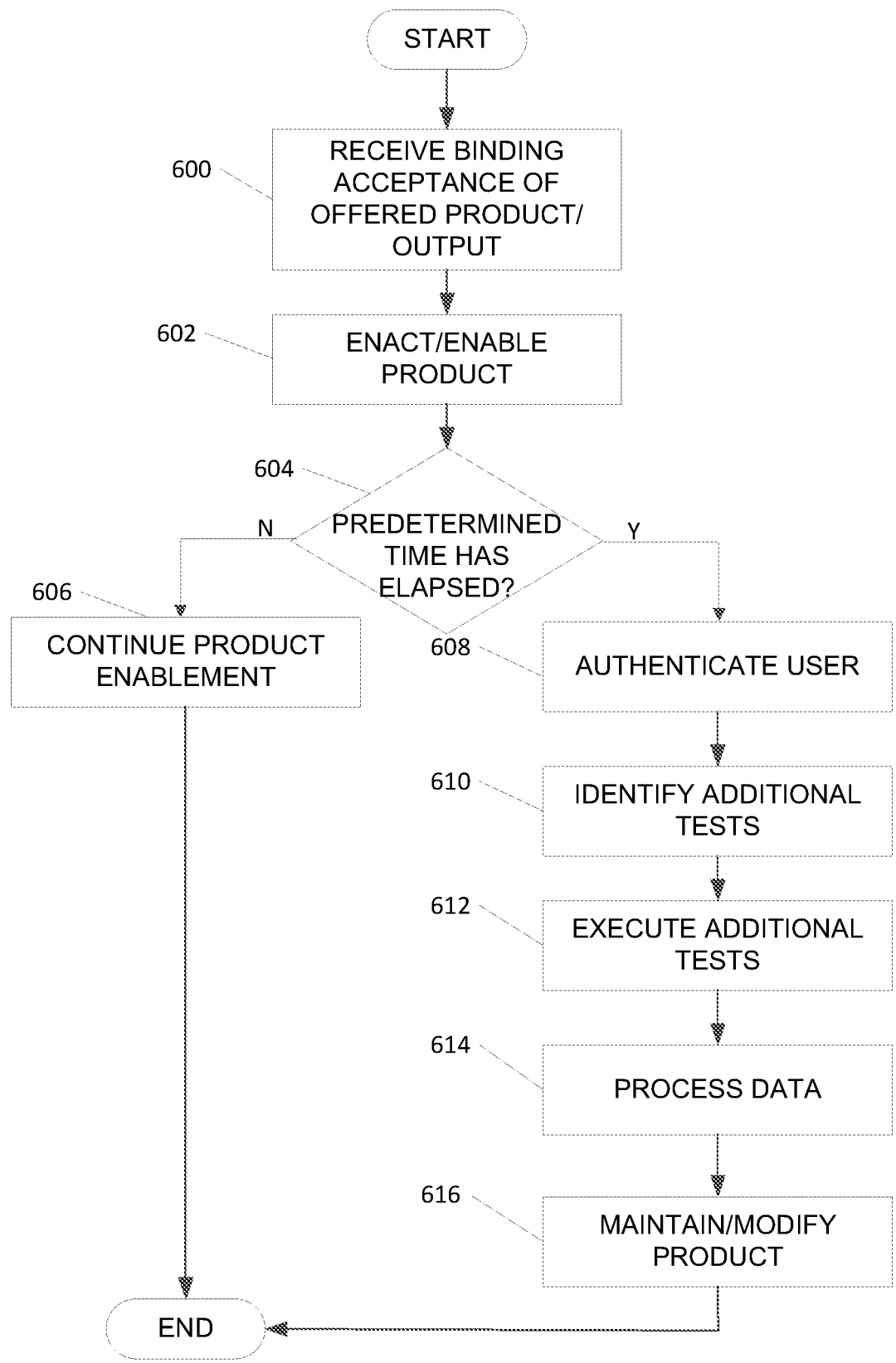
FIG. 6 illustrates one example flow chart illustrating additional interactive condition evaluation test and output generating functions, according to one or more aspects described herein.

FIG. 6 illustrates one example process for renewing a product using interactive condition evaluation tests according to one or more aspects described herein. The steps described with respect to FIG. 6 may be performed by one or more of the various devices described herein, such as the interactive test generation and control computing platform 110, the interactive test generation and control server 210, remote user mobile computing device, and the like. In some examples, one or more of the processes or steps described may be performed in real-time or near real-time.

In step 600, a binding acceptance of an offered product or generated output may be received. In some examples, upon generating and displaying an output to a user, the user may have an option to select to accept an offer associated with the output. In some arrangements, accepting the offer may be a binding agreement and, for instance, may be performed without conventional underwriting processes. In step 602, based on the binding acceptance, the product or generated output may be enabled or enacted. For instance, if the generated output is an insurance policy, acceptance of the binding offer may cause the policy to go into effect.

In step 604, a determination may be made as to whether a predetermined time period has elapsed. For example, the selected product or output may be enacted for a predetermined time period or term. Upon expiration of that term, the product may be cancelled if it is not renewed. Accordingly, in advance of the product being cancelled, and after a predetermined time (e.g., a predetermined time less than the term of the product) system may offer the user an option to renew. Accordingly, the system may determine whether the predetermined time period less than the term of the product has elapsed. If not, the product may remain enabled or enacted in step 606.

If, in step 604, the time period has elapsed, the user may renew the product. In step 608, the user may be authenticated to the system. For instance, a notification may be transmitted to the user requesting the user to login to the system for renewal. In some examples, logging in for renewal may include determining whether user authenticating credentials match pre-stored user authenticating credentials. In some examples, credentials may include username and password, biometric data such as fingerprint, iris scan, facial recognition, and the like.

In step 610, one or more interactive condition evaluation tests may be identified to determine whether the user is eligible to renew, parameters of the renewal, and the like. Similar to other aspects described herein, the interactive condition evaluation tests may be identified based on user information, current product, and the like.

In step 612, the additional tests may be executed. Similar to other arrangements described herein, the additional tests may be executed via a computing device of the user (e.g., remote user mobile computing device 170).

In step 614, data may be collected from test execution and may be processed, for instance, using one or more machine learning datasets. In step 616, based on the processed data, an output may be generated and displayed to the user. In some examples, the output may include an offer or recommendation to maintain or renew the product currently enabled or to modify the product (e.g., obtain a different product, modify one or more parameters of the product, and the like).

Figure 7:
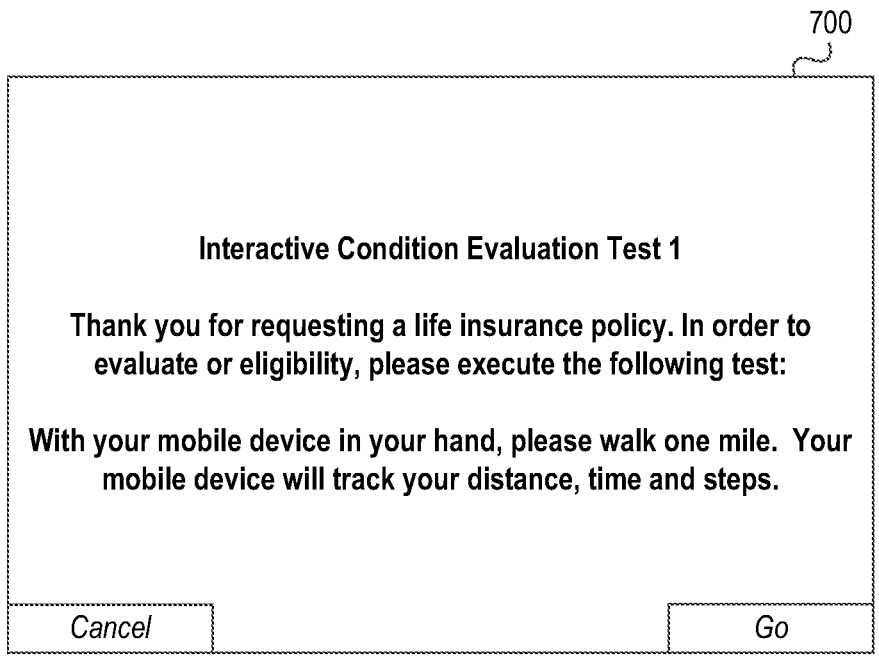
FIG. 7 illustrates one example user interface for executing an interactive condition evaluation test, according to one or more aspects described herein.

FIG. 7 illustrates one example user interface that may be generated and transmitted to a mobile device of a user. The user interface 700 may include identification of a first test, instructions for performing the first test, and the like. The user may initiate the test by selecting "GO" or other option.

Figure 8:
FIG. 8 illustrates one example user interface for displaying a generated output, according to one or more aspects described herein.

FIG. 8 illustrates one example user interface providing a generated output. The interface 800 may include an indication of the product for which the user is eligible or product being offered, as well as a cost associated with the product. In some examples, a link may be provided to additional information, parameters, term, conditions, and the like. The interface 800 may further include an option to accept the offer. Acceptance of the offer may bind the user in real-time, in at least some examples.

FIG. 9 illustrates a block diagram of a computing device (or system) 901 in a computer system 900 that may be used according to one or more illustrative embodiments of the disclosure. The computing device 901 may have a processor 903 for controlling overall operation of the computing device 901 and its associated components, including RAM 905, ROM 907, input/output module 909, and memory 915. The computing device 901, along with one or more additional devices (e.g., terminals 950 and 951, security and integration hardware 960) may correspond to any of multiple systems or devices, such as a user personal mobile computing device, computing platform, or a computer server, configured as described herein for collecting data, identifying and executing one or more interactive condition evaluation tests, evaluating data, generating outputs, and the like.

Input/Output (I/O) 909 may include a microphone, keypad, touch screen, and/or stylus through which a user of the computing device 901 may provide input, and may also include one or more of a speaker for providing audio output and a video display device for providing textual, audiovisual and/or graphical output. Software may be stored within memory 915 and/or storage to provide instructions to processor 903 for enabling computing device 901 to perform various actions. For example, memory 915 may store software used by the computing device 901, such as an operating system 917, application programs 919, and an associated internal database 921. The various hardware memory units in memory 915 may include volatile and nonvolatile, removable and non-removable media implemented in any method or technology for storage of information such as computer readable instructions, data structures, program modules or other data. Certain devices/systems within interactive test generation and control computing system may have minimum hardware requirements in order to support sufficient storage capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) may be used in a device 901 (e.g., a mobile computing device 901, interactive test generation and control server 901, external server 901, etc.), in order to store and execute interactive test generation and control software application, execute tests, collect and analyze data, generate outputs, generate recommendations and/or incentives, etc. Memory 915 also may include one or more physical persistent memory devices and/or one or more non-persistent memory devices. Memory 915 may include, but is not limited to, random access memory (RAM) 905, read only memory (ROM) 907, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 903.

Processor 903 may include a single central processing unit (CPU), which may be a single-core or multi-core processor (e.g., dual-core, quad-core, etc.), or may include multiple CPUs. Processor(s) 903 may have various bit sizes (e.g., 16-bit, 32-bit, 64-bit, 96-bit, 128-bit, etc.) and various processor speeds (ranging from 100 MHz to 5 Ghz or faster). Processor(s) 903 and its associated components may allow the system 901 to execute a series of computer-readable instructions, for example, to identify interactive condition evaluation tests, executing tests, collecting and analyzing data, generating outputs, and the like.

The computing device (e.g., a mobile computing device, computing platform, server, external server, etc.) may operate in a networked environment 900 supporting connections to one or more remote computers, such as terminals 950 and 951. The terminals 950 and 951 may be personal computers, servers (e.g., web servers, database servers), or mobile communication devices (e.g., mobile phones, portable computing devices, on-board vehicle-based computing systems, and the like), and may include some or all of the elements described above with respect to the computing device 901. The network connections depicted in FIG. 9 include a local area network (LAN) 925 and a wide area network (WAN) 929, and a wireless telecommunications network 933, but may also include other networks. When used in a LAN networking environment, the computing device 901 may be connected to the LAN 925 through a network interface or adapter 923. When used in a WAN networking environment, the device 901 may include a modem 927 or other means for establishing communications over the WAN 929, such as network 931 (e.g., the Internet). When used in a wireless telecommunications network 933, the device 901 may include one or more transceivers, digital signal processors, and additional circuitry and software for communicating with wireless computing devices 940 (e.g., mobile phones, portable computing devices, on-board vehicle-based computing systems, etc.) via one or more network devices 935 (e.g., base transceiver stations) in the wireless network 933.

Also illustrated in FIG. 9 is a security and integration layer 960, through which communications may be sent and managed between the device 901 (e.g., a user's personal mobile device, an interactive test generation and control computing platform or server, etc.) and the remote devices (950 and 951) and remote networks (925, 929, and 933). The security and integration layer 960 may comprise one or more separate computing devices, such as web servers, authentication servers, and/or various networking components (e.g., firewalls, routers, gateways, load balancers, etc.), having some or all of the elements described above with respect to the computing device 901. As an example, a security and integration layer 960 of a mobile computing device, computing platform, or a server operated by an insurance provider, financial institution, governmental entity, or other organization, may comprise a set of web application servers configured to use secure protocols and to insulate the server 901 from external devices 950 and 951. In some cases, the security and integration layer 960 may correspond to a set of dedicated hardware and/or software operating at the same physical location and under the control of same entities as driving data analysis server 901. For example, layer 960 may correspond to one or more dedicated web servers and network hardware in an organizational datacenter or in a cloud infrastructure supporting a cloud-based driving data analysis system. In other examples, the security and integration layer 960 may correspond to separate hardware and software components which may be operated at a separate physical location and/or by a separate entity.

As discussed below, the data transferred to and from various devices in the computing system 900 may include secure and sensitive data, such as device usage data, application usage data, medical or personal information, test result data, and the like. Therefore, it may be desirable to protect transmissions of such data by using secure network protocols and encryption, and also to protect the integrity of the data when stored on in a database or other storage in a mobile device, interactive test generation and control computing platform or server and other computing devices in the system 900, by using the security and integration layer 960 to authenticate users and restrict access to unknown or unauthorized users. In various implementations, security and integration layer 960 may provide, for example, a file-based integration scheme or a service-based integration scheme for transmitting data between the various devices in a system 900. Data may be transmitted through the security and integration layer 960, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption. In other examples, one or more web services may be implemented within the various devices 901 in the system 900 and/or the security and integration layer 960. The web services may be accessed by authorized external devices and users to support input, extraction, and manipulation of the data (e.g., device usage data, location data, vehicle data, etc.) between the various devices 901 in the system 900. Web services built to support system 900 may be cross-domain and/or cross-platform, and may be built for enterprise use. Such web services may be developed in accordance with various web service standards, such as the Web Service Interoperability (WS-I) guidelines. In some examples, a movement data and/or driving data web service may be implemented in the security and integration layer 960 using the Secure Sockets Layer (SSL) or Transport Layer Security (TLS) protocol to provide secure connections between servers 901 and various clients 950 and 951 (e.g., mobile devices, data analysis servers, etc.). SSL or TLS may use HTTP or HTTPS to provide authentication and confidentiality. In other examples, such web services may be implemented using the WS-Security standard, which provides for secure SOAP messages using XML encryption. In still other examples, the security and integration layer 960 may include specialized hardware for providing secure web services. For example, secure network appliances in the security and integration layer 960 may include built-in features such as hardware-accelerated SSL and HTTPS, WS-Security, and firewalls. Such specialized hardware may be installed and configured in the security and integration layer 960 in front of the web servers, so that any external devices may communicate directly with the specialized hardware.

Although not shown in FIG. 9, various elements within memory 915 or other components in system 900, may include one or more caches, for example, CPU caches used by the processing unit 903, page caches used by the operating system 917, disk caches of a hard drive, and/or database caches used to cache content from database 921. For embodiments including a CPU cache, the CPU cache may be used by one or more processors in the processing unit 903 to reduce memory latency and access time. In such examples, a processor 903 may retrieve data from or write data to the CPU cache rather than reading/writing to memory 915, which may improve the speed of these operations. In some examples, a database cache may be created in which certain data from a database 921 (e.g., interactive condition evaluation test result database, internal data database, external data database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of performing functions describes herein.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computer devices and system components described herein may be configured to communicate using any of these network protocols or technologies.

Additionally, one or more application programs 919 may be used by the various computing devices 901 within an interactive test generation and control computing system 900 (e.g., software applications, etc.), including computer executable instructions for identifying one or more products, identifying one or more interactive condition evaluation tests, executing interactive condition evaluation tests, collecting data, analyzing data, and the like, as described herein.

As discussed herein, various examples for generating an output based on different types of data from different sources are described. In some examples, machine learning may be used to generate one or more outputs. Using data from various different sources, as well as different types of data, may provide more accurate predictions of risk, mortality, and the like, in order to generate and offer outputs that are more closely tailored to a user's needs.

Further, using the various types of data, as well as machine learning, may allow and entity generating an output to better align pricing with a determined risk. In conventional systems, it may take several years to evaluate outputs, such as a determined risk for a particular user, a predicted mortality, or the like. By processing great volumes of data to generate machine learning datasets, validation of risk predictions or assumptions, and the like may be performed much more quickly which ultimately may allow for pricing of products (e.g., insurance policies, and the like) at a more granular level.

As discussed, one or more interactive condition evaluation tests may be used to collect data associated with a user, assess conditions of the user, determine whether a user is eligible for a product, and/or generate an output (e.g., an insurance policy to offer, a premium for an insurance policy, a discount or incentive, or the like). Below are several example interactive condition evaluation tests that may be used with one or more arrangements described herein. Various other tests may be used without departing from the invention and nothing in the examples below should be viewed as limiting the interactive condition evaluation tests to only these examples.

In one example, an interactive condition evaluation test may include evaluating mobility of a user. Accordingly, the interactive test generation and control computing platform 110 may generate a user interface including instructions for executing a mobility test using a mobile device of the user. The user may receive the interface which may be displayed on the mobile device. In some examples, the test may include instructing a user to walk, run, jog, or the like, a predetermined distance. Sensors within the mobile device may track the distance walked, time for walking the distance, pace of the user, and the like. In some examples, data related to heart rate of the user, pulse of the user, and the like, may also be collected by one or more sensors in the mobile device. This information may then be transmitted to the interactive test generation and control computing platform 110 for processing and analysis.

In another example, a user may be instructed to walk, run, jog, or the like, on a treadmill for a predetermined time, at a predetermined pace, or the like, while carrying the user's mobile device. Sensors within the device may detect and/or collect data associated with performance of the test, heart rate, pulse, and the like, and this information may be transmitted to the interactive test generation and control computing platform 110 for processing and analysis.

In some arrangements, for either of the above-described example interactive tests, video may be captured of the user while performing the test. This video may be further evaluated to determine a gait of user, how easily the user managed the interactive test, or the like.

In other example interactive tests, a user may be instructed to perform one or more other physical functions (e.g., outside of walking, running or the like). For instance, a user may be requested to hold his or her arms in front of his or her body for as long as possible while holding the mobile device. One or more sensors within the mobile device may collect data associated with a position of the mobile device, time in a particular position, and the like, and this information may be transmitted to the interactive test generation and control computing platform 110 for processing and analysis.

In some examples, similar physical tests may be performed with a user's legs (e.g., sit in chair and extend legs).

In some examples, one or more interactive tests may test a reflex of a user. For instance, an image may be displayed on a mobile device of a user with instructions to touch one or more icons indicating a certain item (e.g., a plurality of icons are displayed, touch or select all that are a particular object). The sensors and/or other mobile device components may detect not only how many correct answers the user provided but also how quickly the user was able to respond (e.g., how quickly the user could touch the screen). This data may then be transmitted to the interactive test generation and control computing platform 110 for processing an analysis.

In another example interactive condition evaluation test for reflexes, the user may be instructed to touch a display of the mobile device as quickly as possible upon seeing a particular prompt. The mobile device may then collect data associated with how quickly the user touched the display and may transmit that data for processing and analysis.

Additional interactive condition evaluation tests may be directed to evaluating a user's recall. For instance, a user may be provided with a list of words that they may view for a predetermined time period. After the time period expires, the user may be requested to input as many words as he or she can remember. The words may be input via a keyboard (e.g., virtual or physical) or spoken.

In some examples, one or more interactive condition evaluation tests may be used to evaluate a lung capacity or respiration of a user. For instance, a tobacco user may have a reduced lung capacity, increased respiration rate, or the like. Accordingly, one or more interactive condition evaluation tests may include having a user exhale onto a mobile device and one or more sensors may be detect a number of exhalations, a velocity of the breath, a rate of exhalations, and the like. In some examples, the user may exhale onto a microphone of the mobile device and the audio received may be processed to determine a strength of exhale, number of exhalations, and the like. In some examples, one or more test may request a user to exhale for a predetermined amount of time while positioned a predetermined distance from the mobile device. This information may be transmitted to the interactive test generation and control computing platform 110 for processing and analysis.

In some examples, one or more interactive condition evaluation tests may include monitoring sleep habits of a user. This data may then be transmitted for processing and analysis.

In some examples, one or more interactive condition evaluation tests may including requesting a user to capture one or more images of particular body parts, or the like. For instance, images of the user may be used to determine height, weight, overall health appearance, and the like. In some examples, the user may be requested to submit particular images. For instance, a close up image of an eye of a user may be used to determine one or more health issues, such as coronary disease, hypertension, diabetes, and the like. u In some examples, the system may generate a plurality of tests for execution. A user may, in some examples, complete some or all of the tests. If the user completes fewer than all of the tests, the output generated may be impacted by completion of fewer than all of the identified tests (e.g., output may include a higher premium for a policy than a user completing all tests, discount or incentive may be different from a user who completed all tests, or the like).

Although various aspects described herein are described as being executed by a mobile device of a user, a mobile device may, in some examples, include a wearable device, such as a fitness tracker. One or more tests may be executed via the fitness tracker, data may be collected and transmitted, and the like. In some examples, data from a fitness tracker or other wearable device may be used in combination with other data (e.g., may be used as data from an external source, collected, aggregated and processed, as discussed herein).

Data from sources other than the interactive condition evaluation tests may also be used, as discussed herein. For instance, data from internal sources and/or external sources may be used to evaluate risk, generate outputs, provide offers, and the like.

For instance, in some examples, data associated with usage of a mobile device may be collected and used in analyzing eligibility, generating outputs, and the like. For instance, types of applications accessed by a user, how often applications are accessed, and the like, may be collected and used in the analysis. For example, if a user executes one or more health or fitness applications on a mobile device, that may indicate a healthy lifestyle. Alternatively, if the mobile device is often used for streaming video, that may indicated a more sedentary lifestyle. These factors may be used to evaluate eligibility, determine an output, or the like.

As discussed herein, various types of internal data may be collected and used in making various output determinations. For instance, if the entity implementing the system is an insurance provider, data associated with home insurance, auto insurance, life insurance, and the like may be used. In some examples, historical data such as claims data, and the like, may be used in generating one or more machine learning datasets. Data associated with a particular user requesting a product may also be extracted and used to generate an output. For example, user claim history, vehicle operational data or driving behaviors (e.g., as collected from a vehicle of the user, mobile device of the user, or the like), may be used.

As also discussed herein, various types of external data may be collected and used in making various output determinations. In some examples, the external data may be received from one or more sources external to an entity implementing the system. The external sources may include publicly available information, anonymous information, information collected with permission of the user, and the like. Some examples of external data are provided below. However, various other types of external data may be collected and used without departing from the invention and the examples below should not be viewed as limiting external data to only these types of data.

In some examples, consumer data such as transaction data and the like may be used. For instance, data collected via a loyalty program at grocery stores, department stores, and the like, may be used to evaluate a lifestyle of user. Data such as types of purchases made, locations of purchase, frequency of purchase, amount of purchase, and the like may be considered. In some examples, purchases made at a grocery store (e.g., healthy foods, cigarettes, alcohol, or the like) may be collected and evaluated to generate one or more outputs.

In some examples, external data such as medical information of the user may be collected and used in the analysis. This data may be collected with permission of the user and may include prescriptions used, medical diagnosis, recent lab results, recent results of a physical examination, family medical history, and the like.

In some arrangements, other behavioral data may be used. For instance, whether a user has a membership to a gym, how often the user visits the gym, and the like, may be used.

In some examples, global positioning system data may be used to determine or verify a position of a user (e.g., user visits a gym 5 days/week). Additionally or alternatively, detecting behaviors such as marathon running, 5K running, or the like, may be detected from sensor data, as well as time, pace, and the like. This data may be collected and used in evaluation for generating outputs.

Data associated with occupation and/or hobbies may also be considered. For instance, detection of, for instance, skydiving, as a hobby (e.g., based on altimeter sensor data from a mobile device) may indicate a risk factor for a user. In some examples, data associated with an occupation may be collected. For instance, detection of frequent changes in altitude, speed, and the like, may indicate a user is a flight attendant, pilot, or the like. This information may be used in evaluation.

In some examples, user data may be collected over a period of time to determine how sedentary a life a user lives. For instance, the movement of the mobile device may be tracked via one or more sensors and that information may be transmitted for processing and analysis. In some examples, this data may be collected during an eligibility evaluation process (e.g., before an output is generated, an offer is provided, or the like). Additionally or alternatively, the data may be collected during a term of, for instance, an insurance policy, to monitor a user's lifestyle. In some examples, historical data from a time prior to the user requesting a product may be collected and evaluated to identify potential risk. Data may also be collected after the user has purchased the product to continue to evaluate risk. This continuous or continued collection may be also be used for dynamic pricing (e.g., pricing that may change based on detected behaviors) and/or for renewal of a product.

As discussed herein, in some examples, a user may accept a generated output or offer and a binding agreement may be made. In some arrangements, one or more of the data collection, processing, offer and acceptance may be performed in real-time. In some examples, the binding agreement may be based solely on the data collected from interactive condition evaluation tests, internal data, external data, and the like (e.g., without traditional underwriting, physical examination or the like). In other examples, a user may be provided with an output having a first price. Acceptance of the offer may include the user agreeing to the first price, however, an incentive may be generated for a user to provide additional information, such as recent medical examination results, lab work, or the like. Accordingly, a rebate, refund, credit, or the like, may be offered for providing this additional information.

In some examples, a user may also permit an entity to use the collected data, generated outputs, test results, and the like in determining eligibility for one or more other products. For instance, a system may generate a recommended other product (e.g., long term care insurance, auto insurance, or the like) and the data collected may be used to evaluation risk, eligibility, and the like. In some examples, the data may be used to evaluate requests made by the user for additional products.

As discussed above, biometric data such as fingerprints and the like, and/or facial recognition data may be used to authenticate a user, provide additional functionality, and the like. For instance, upon initiating an interactive condition evaluation test, a user may be requested to capture an image of himself or herself. Facial recognition may then be used to confirm that the image captured corresponding to the user. In some examples, public records may be used to confirm this information. In other examples, the user may be asked to provide an image of, for instance, a driver's license. This may then be compared to a captured image to verify the identity of the user.

In some arrangements, fingerprint or other biometric data may also be used. For instance, a user may submit a fingerprint with acceptance of an offer, for an insurance policy or the like. If a claim is then made against the policy, or a modification is requested, the user may authenticate by submitting a fingerprint.

In another example, a beneficiary of an insurance policy may be identified by his or her fingerprint. Accordingly, the beneficiary may submit the fingerprint upon a user purchasing the policy. The beneficiary may then submit a fingerprint to submit a claim.

In some arrangements, one or more aspects described herein may be embodied in an application executing on a computing device of a user. In some arrangements, upon opening the application, various functionality may be enabled. For instance, sensors may be activated, permission may be given to collect data, and the like. Although various aspects described herein are described with respect to life insurance policies, one or more aspects described herein may be used to evaluate eligibility for other products or services, such as auto insurance, homeowners insurance, long term care insurance, and the like.

One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, Application-Specific Integrated Circuits (ASICs), Field Programmable Gate Arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. Furthermore, such aspects may take the form of a computer program product stored by one or more computer-readable storage media having computer-readable program code, or instructions, embodied in or on the storage media. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may be and/or include one or more non-transitory computer-readable media.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, one or more steps described with respect to one figure may be used in combination with one or more steps described with respect to another figure, and/or one or more depicted steps may be optional in accordance with aspects of the disclosure.

What is claimed is:

1. A system comprising:
    a processing unit comprising a processor; and
    a memory unit storing computer-executable instructions, which when executed by the processing unit, cause the processor to:
        identify, based on a request for a product, one or more products, the request received from a user computing device;
        identify, based on the one or more products, one or more interactive condition evaluation tests to determine an eligibility for the one or more products;
        generate a first user interface, the first user interface presenting instructions for executing the one or more interactive condition evaluation tests;
        transmit, to the user computing device, the first user interface to cause the user computing device to output the first user interface;
        collect data from one or more sensors associated with the user computing device in accordance with the one or more interactive condition evaluation tests;
        process, based on one or more machine learning datasets, the data to determine an output, the output including an indication of the eligibility for the product;
        generate a second user interface including the output; and
        transmit the second user interface to the user computing device to cause the user computing device to output the second user interface to present the indication.

2. The system of claim 1, wherein the request indicates the one or more products.

3. The system of claim 1, wherein the request includes information associated with a user.

4. The system of claim 3, wherein the information includes one or more of a name and contact information.

5. The system of claim 1, wherein the one or more interactive condition evaluation tests includes a timed treadmill test.

6. The system of claim 1, wherein the one or more sensors include one or more of an accelerometer, a global positioning system (GPS) sensor, a gyroscope, a pressure sensor, a humidity sensor, a pedometer, a heart rate sensor, a pulse sensor, a breathing sensor, and an image capturing device.

7. The system of claim 1, wherein the output includes a cost associated with the one or more products.

8. A method comprising:
    identifying, based on a request, one or more products, the request received from a computing device associated with a user;
    identifying, based on the one or more products, one or more interactive condition evaluation tests to determine eligibility of the user to purchase the one or more products;
    generating a first user interface, the first user interface indicating instructions for executing the one or more interactive condition evaluation tests;
    transmitting, to the computing device, the first user interface to cause the computing device to present the first user interface;
    collecting data from one or more sensors associated with the computing device in accordance with the one or more interactive condition evaluation tests;
    processing, based on one or more machine learning datasets, the data to determine the eligibility of the user;
    generating a second user interface presenting an indication of the eligibility of the user; and
    transmitting the second user interface to the computing device to cause the computing device to output the second user interface to present the indication.

9. The method of claim 8, wherein the request includes a selection of the one or more products.

10. The method of claim 8, wherein the request includes information associated with the user.

11. The method of claim 10, wherein the information includes one or more of a name and contact information.

12. The method of claim 8, wherein the one or more interactive condition evaluation tests includes a treadmill test.

13. The method of claim 8, wherein the one or more sensors include one or more of an accelerometer, a global positioning system (GPS) sensor, a gyroscope, a pressure sensor, a humidity sensor, a pedometer, a heart rate sensor, a pulse sensor, a breathing sensor, and an image capturing device.

14. The method of claim 8, wherein the second user interface further indicates a cost associated with the one or more products.

15. One or more non-transitory computer-readable media storing instructions that, when executed by at least one processor, memory, and a communication interface, cause the at least one processor to:
    identify one or more products based on a request for a product, the request received from a computing device;

identify one or more interactive condition evaluation tests to determine an eligibility for the one or more products, the one or more interactive condition evaluation tests based on the one or more products;

generate a first user interface, the first user interface indicating instructions for executing the one or more interactive condition evaluation tests;

transmit, to the computing device, the first user interface to cause the computing device to present the first user interface;

collect data from one or more sensors in accordance with the one or more interactive condition evaluation tests;

process the data to determine an output based on one or more machine learning datasets, the output including a notification of the eligibility for the product;

generate a second user interface including the output; and transmit the second user interface to the computing device to cause the computing device to output the second user interface to present the output.

16. The one or more non-transitory computer-readable media of claim 15, wherein the request indicates the one or more products.

17. The one or more non-transitory computer-readable media of claim 15, wherein the request includes information associated with a user.

18. The one or more non-transitory computer-readable media of claim 17, wherein the information includes one or more of a name and contact information.

19. The one or more non-transitory computer-readable media of claim 15, wherein the one or more interactive condition evaluation tests includes a timed treadmill test.

20. The one or more non-transitory computer-readable media of claim 15, wherein the one or more sensors include one or more of an accelerometer, a global positioning system (GPS) sensor, a gyroscope, a pressure sensor, a humidity sensor, a pedometer, a heart rate sensor, a pulse sensor, a breathing sensor, and an image capturing device.

* * * * *